United States Patent
Dettman et al.

(10) Patent No.: US 10,793,915 B2
(45) Date of Patent: Oct. 6, 2020

(54) CONTEXT DEPENDENT DIAGNOSTICS TEST FOR GUIDING CANCER TREATMENT

(71) Applicant: Eutropics Pharmaceuticals, Inc., Cambridge, MA (US)

(72) Inventors: Elisha J. Dettman, Cambridge, MA (US); Michael H. Cardone, Dorchester, MA (US)

(73) Assignee: Eutropics Pharmaceuticals, Inc., Cambridge, MA (US)

( * ) Notice: Subject to any disclaimer, the term of this patent is extended or adjusted under 35 U.S.C. 154(b) by 218 days.

(21) Appl. No.: 15/542,520

(22) PCT Filed: Jan. 12, 2016

(86) PCT No.: PCT/US2016/013003
§ 371 (c)(1),
(2) Date: Jul. 10, 2017

(87) PCT Pub. No.: WO2016/115105
PCT Pub. Date: Jul. 21, 2016

(65) Prior Publication Data
US 2018/0340229 A1  Nov. 29, 2018

Related U.S. Application Data

(60) Provisional application No. 62/102,499, filed on Jan. 12, 2015.

(51) Int. Cl.
*C12Q 1/6886* (2018.01)
*G16B 40/00* (2019.01)
*G16H 50/50* (2018.01)
*A61P 35/02* (2006.01)
*A61K 31/453* (2006.01)

(52) U.S. Cl.
CPC .......... *C12Q 1/6886* (2013.01); *A61K 31/453* (2013.01); *A61P 35/02* (2018.01); *G16B 40/00* (2019.02); *G16H 50/50* (2018.01); *C12Q 2600/106* (2013.01); *C12Q 2600/118* (2013.01); *C12Q 2600/156* (2013.01); *C12Q 2600/158* (2013.01)

(58) Field of Classification Search
CPC .................................................. C12Q 1/6886
USPC ....................................................... 435/7.23
See application file for complete search history.

(56) References Cited

U.S. PATENT DOCUMENTS

| | | |
|---|---|---|
| 5,856,445 A | 1/1999 | Korsmeyer |
| 5,955,593 A | 9/1999 | Korsmeyer |
| 5,998,583 A | 12/1999 | Korsmeyer |
| 6,165,732 A | 12/2000 | Korsmeyer et al. |
| 6,258,540 B1 | 7/2001 | Lo et al. |
| 6,326,354 B1 | 12/2001 | Gross et al. |
| 7,026,456 B1 | 4/2006 | Gately et al. |
| 7,247,700 B2 | 7/2007 | Korsmeyer et al. |
| 7,723,469 B2 | 5/2010 | Walensky et al. |
| 7,829,662 B2 | 11/2010 | Korsmeyer et al. |
| 7,868,133 B2 | 1/2011 | Korsmeyer et al. |
| 7,871,769 B2 | 1/2011 | Baker et al. |
| 8,168,755 B2 | 5/2012 | Cardone et al. |
| 8,198,405 B2 | 6/2012 | Walensky et al. |
| 8,221,966 B2 | 7/2012 | Letai |
| 8,323,987 B2 | 12/2012 | Threadgill et al. |
| 8,796,418 B2 | 8/2014 | Walensky et al. |
| 8,889,632 B2 | 11/2014 | Bernal et al. |
| 9,273,099 B2 | 3/2016 | Walensky et al. |
| 9,464,115 B2 | 10/2016 | Walensky et al. |
| 9,527,896 B2 | 12/2016 | Bernal et al. |
| 9,540,674 B2 | 1/2017 | Letai |
| 9,856,303 B2 | 1/2018 | Korsmeyer et al. |
| 9,902,759 B2 | 2/2018 | Korsmeyer et al. |
| 2002/0177692 A1 | 11/2002 | Bartel |
| 2003/0073661 A1 | 4/2003 | Matsuyama et al. |
| 2003/0181404 A1 | 9/2003 | Avraham et al. |
| 2004/0241902 A1 | 10/2004 | Wang et al. |
| 2005/0191696 A1 | 9/2005 | Goldmakher et al. |
| 2006/0183687 A1 | 8/2006 | Cory et al. |
| 2008/0104721 A1 | 5/2008 | Barsova et al. |
| 2009/0030005 A1 | 1/2009 | Kamb et al. |
| 2009/0280510 A1 | 11/2009 | Cardone et al. |
| 2010/0015058 A1 | 1/2010 | Li et al. |
| 2011/0008371 A1 | 1/2011 | Michelson |
| 2011/0071042 A1 | 3/2011 | Kim et al. |
| 2011/0154522 A1 | 6/2011 | Korsmeyer et al. |
| 2012/0225794 A1 | 9/2012 | Cardone et al. |
| 2012/0225851 A1 | 9/2012 | Cardone et al. |
| 2013/0079424 A1 | 3/2013 | Gerber et al. |
| 2015/0301053 A1 | 10/2015 | Pierceall et al. |
| 2016/0273020 A1 | 9/2016 | Pierceall et al. |

FOREIGN PATENT DOCUMENTS

| | | |
|---|---|---|
| CN | 1583776 A | 2/2005 |
| WO | 96/13614 A1 | 5/1996 |
| WO | 1996015263 A1 | 5/1996 |

(Continued)

OTHER PUBLICATIONS

Karp et al (Clin Cancer Res, 2007, 13(15): 4467-4473).*
Foight et al (ACS Chem Biol, 2014, 9: 1962-1968).*
Brunelle et al (JCB, 2009, 187(3): 429-442).*
Zeng et al (Blood, 2012, 120(13): 2679-2689).*
Mills et al (PNAS, 2008, 105(31): 10853-10858).*
'KG-la (ATCC® CCL-246.1™) ATCC Product Sheet, 3 pages. (2013).
Adlard, et al., "Prediction of the response of colorectal cancer to systemic therapy," Lancet Oncol. 3:75-82 (2002).
Bodet, et al., "BH3-only protein Bik is involved in both apoptosis induction and sensitivity to oxidative stress in multiple myeloma," Br. J. Cancer 103:1808-1814 (2010).

(Continued)

*Primary Examiner* — Sean E Aeder
(74) *Attorney, Agent, or Firm* — Morgan, Lewis & Bockius LLP

(57) ABSTRACT

The present disclosure provides diagnostic methods that are relevant to various cancers and which comprise improvements on a BH3 profiling diagnostic method.

9 Claims, 21 Drawing Sheets
Specification includes a Sequence Listing.

(56) References Cited

FOREIGN PATENT DOCUMENTS

| | | |
|---|---|---|
| WO | 1998/009643 A1 | 3/1998 |
| WO | 1998/009980 A1 | 3/1998 |
| WO | 1998/017682 A1 | 4/1998 |
| WO | 1999/016787 A9 | 4/1999 |
| WO | 2000/006187 A2 | 2/2000 |
| WO | 2000/011162 A1 | 3/2000 |
| WO | 2002/005835 A2 | 1/2002 |
| WO | 2003/057158 A2 | 7/2003 |
| WO | 2004/022580 A2 | 3/2004 |
| WO | 2004/087887 A2 | 10/2004 |
| WO | 2005/044839 A2 | 5/2005 |
| WO | 2007/123791 A9 | 2/2008 |
| WO | 2008/021484 A2 | 8/2010 |
| WO | 2010/093742 A1 | 7/2011 |
| WO | 2011/088137 A2 | 7/2011 |
| WO | 2012/122370 A2 | 9/2012 |
| WO | 2013/138702 A2 | 9/2013 |
| WO | 2013170176 A2 | 11/2013 |
| WO | 2014/047342 A1 | 3/2014 |
| WO | 2015/042249 A1 | 3/2015 |
| WO | 2016/176288 A1 | 3/2016 |
| WO | 2016/176299 A1 | 3/2016 |

OTHER PUBLICATIONS

Campbell, et al., "General properties and applications of monoclonal antibodies," Monoclonal Antibody Technology, pp. 1-32 (1984).
Certo, et al., "Mitochondria Primed by Death Signals Determine Cellular Addiction to Antiapoptotic BCL-2 Family Members," Cancel Cell 9:351-365 (May 2006).
Chonghaile, et al., "Mitochondrial Apoptotic Priming Measured by BH3 Profiling Regulates Clinical Response to Chemotherapy in Myeloma and Acute Lymphoblastic Leukemia and Explains Therapeutic Index," Abstract 1142, 53rd ASH Annual Meeting and Exposition, Dec. 10-13, 2011, American Society of Hematology.
Chonghaile, et al., "Pretreatment Mitochondrial Priming Correlates with Clinical Response to Cytotoxic Chemotherapy," Science 334:1129-1133, including supporting material (2011).
Cimmino, et al., "miR-15 and miR-16 induce apoptosis by targeting BCL2," Proc. Natl. Acad. Sci. USA 102 (39):13944-13945 (2005).
Colman, "Effects of amino acid sequence changes on antibody-antigen interactions," Res. Immunol. 145"33-36 (1994).
Davids, et al., "BH3 Profiling Demonstrates That Restoration of Apoptotic Priming Contributes to Increased Sensitivity to P13K Inhibition on Stroma-Exposed Chronic Lymphocytic Leukemia Cells," Blood 118: Abstract 974 (2011).
Del Gaizo Moore, et al., "BH3 profiling—measuring intergrated function of the mitochondrial apoptotic to predict cell fate decisions," Cancer Lett. 332(2):202-205 (2013).
Del Gaizo Moore, et al., "Chronic lymphocytic leukemia requires BCL2 to sequester prodeath BIM, explaining sensitivity to BCL2 antagonist ABT-737," J. Clin. Invest. 117(1):112-121 (2007).
Deng, et al., "BH3 Profiling Identifies Three Distinct Classes of Apoptotic Blocks to Predict Response to ABT-737 and Conventional Chemotherapeutic Agents," Cancel Cell 12:171-185 (2007).
Hann, et al., "Therapeutic Efficacy of ABT-737, a Selective Inhibitor of BCL-2, in Small Cell Lung Cancer," Cancer Res. 68:2321-2328 (2008).
Kasper, et al., "Targeting MCL-1 sensitizes FLT3-ITD-positive leukemias to cytotoxic therapies," Blood Cancer J. 2:10 pages (2012).
Letai, et al., "Antiapoptotic BCL-2 is required for maintenance of a model leukemia," Cancer Cell, 6:241-249 (2004).
Letai et al., "Diagnosing and exploiting cancer's addiction to blocks in apoptosis," Nat. Rev. Cancer 8:121-132 (2008).
Maccallum et al., "Antibody-antigen Interactions: Contact Analysis and Binding Site Topography," J. Mol. Biol. 262:732-745 (1996).
Miller, et al, "Therapeutic Strategies to Enhance the Anticancer Efficacy of Histone Deacetylase Inhibitors," J. Biomed. Biotechnol. 2011:17 pages (2011).
Paoluzzi, et al., "The BH3-only mimetic ABT-737 synergizes the antineoplastic activity of proteasome inhibitors in lymphoid malignancies," Blood 112:2906-2916 (2008).
Paul, "Fundamental Immunology," 3rd Edition, Raven Press, Ltd., pp. 292-295 (1993).
Pode-Shakked, et al., "Developmental tumourigenesis: NCAM as a putative marker for the malignant renal stem/progenitor cell population," J. Cell. Mol. Med. 13(88):1792-1808 (2009).
Pritzker, et al., "Cancer Biomarkers: Easier Said Than Done," Clin. Chem. 48(8):1147-1150 (2002).
Raychaudhuri, et al., "Low probability Bid-Bax reaction generates heterogeneit in apoptosis resistance of cancer and cancer stem cells," arXiv:1108.209 [q-bio.MN], 17 pages (2011).
Rollins-Raval and Roth, "The value of immunohistochemistry for CD14, CD123, CD33, myeloperoxidase and CD68R in the diagnosis of acute and chronic myelomonocytic leukaemias," Histopathology 60:933-942 (2012).
Rudikoff, et al., "Single amino acid substitution altering antigen-binding specificity," Proc. Natl. Acad. Sci. USA 79:1979-1983 (1982).
Sinicrope, et al., "Proapoptotic Bad and Bid Protein Expression Predict Survival in Stages II and III Colon Cancers," Clin. Canc. Res. 14(13):4128-4133 (2008).
Sinicrope, et al., "Prognostic Impact of Bim, Puma, and Noxa Expression in Human Colon Carcinomas," Clin. Canc. Res. 14(18):5810-5818 (2008).
Stewart, et al., "The MCL-1 BH3 Helix is an Exclusive MCL-1 inhibitor and Apoptosis Sensitizer," Nat. Chem. Biol. 6(8):595-601 (2010).
Taussig, et al., "Anti-CD38 antibody-mediated clearance of human repopulating cells masks the heterogeneity of leukemia-initiating cells," Blood 112:568-575 (2008).
Thomenius, et al., "Using BH3 Profiling As a Predictive Indicator for Myeloma Patient Response to Bortezomib," Blood 118(21):abstract No. 3952 (2011).
Valencia, et al., "A new reliable fluorescence in situ hybridization method for identifying multiple specific cytogenetic abnormalities in acute myeloid leukemia," Leukemia & Lymphoma 51(4):680-685 (2010).
Vo, "Mitchondrial Priming Determines Chemotherapeutic Response in Acute Myeloid Leukemia," Disseration, Harvard University, UMI No. 3514220, 119 pages (2012).
Vo, "Relative Mitochondrial Priming of Myeloblasts and Normal HCSs Detemines Chemotherapeutic Success in AML," Cell 151(2):344-355 (2012).
Weniger, et al., "Treatment-Induced Oxidative Stress and Cellular Antioxidant Capacity Determine Response to Bortezomib in Mantel Cell Lymphoma," Clin. Canc. Res. 17(15):5101-5112 (2011).
Liu, et al., "The Structure of a Bcl-xL/Bim Fragment Complex: Implications for Bim Function," Immunity, vol. 19, 341-352, Sep. 2003.
Mohammad et al., "Nonpeptidic Small-Molecule Inhibitor of Bcl-2 and BCl-XL, (−)—Gossypol, Enhances Biological Effect of Genistein Against BxPC-3 Human Pancreatic Cancer Cell Line," Pancreas, vol. 31, No. 4, Nov. 2005, pp. 317-324.
Piercall et al., "BH3 Profiling Discriminates Response to Cytarabine-Based Treatment of Acute Myelogenous Leukemia," Mol Cancer Ther (Dec. 2013) vol. 12, No. 12, pp. 2940-2949.
International Search Report and Written Opinion, International Application No. PCT/US2016/013003, dated Mar. 28, 2016, 4 pages.

\* cited by examiner

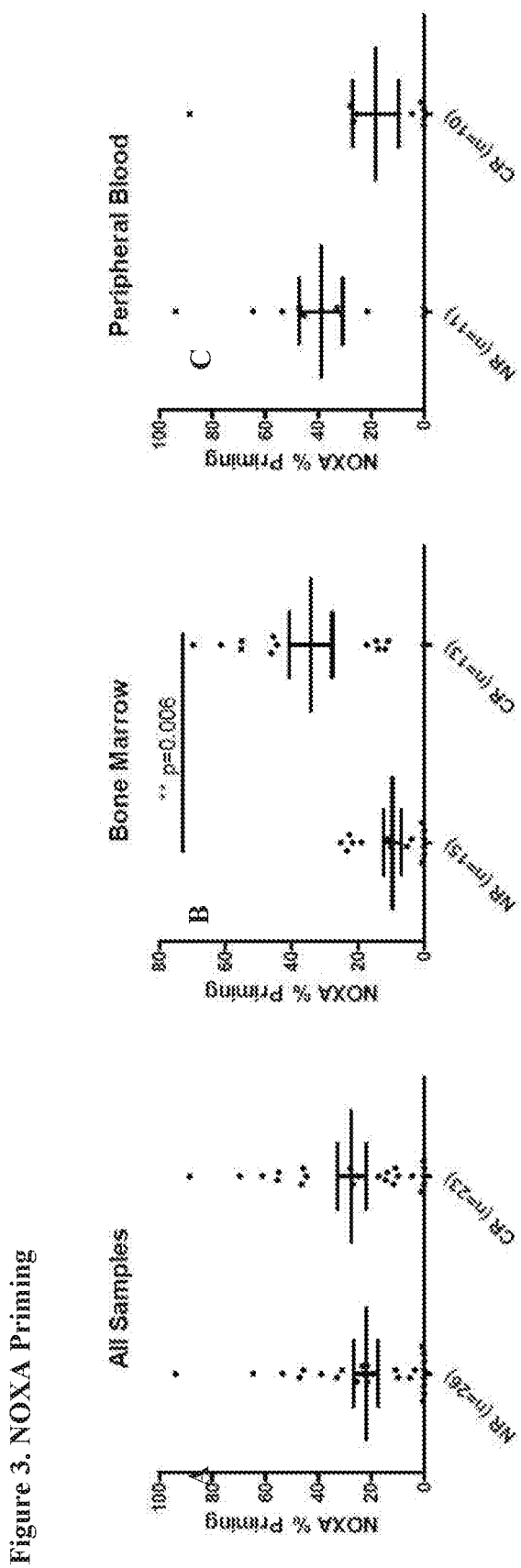

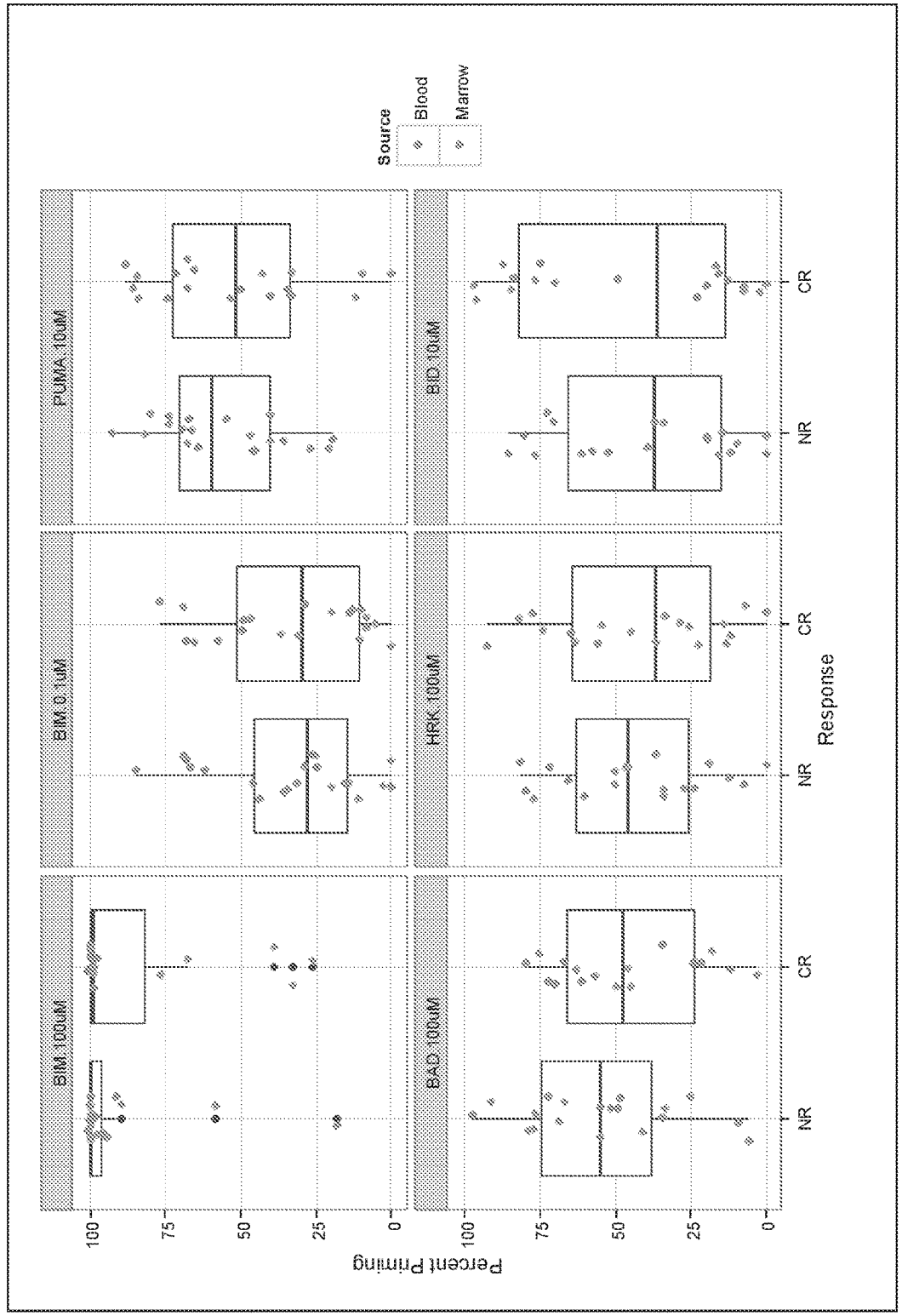
Figure 5B: Lack of correlation between assay readouts in mixed peripheral and bone marrow blood samples

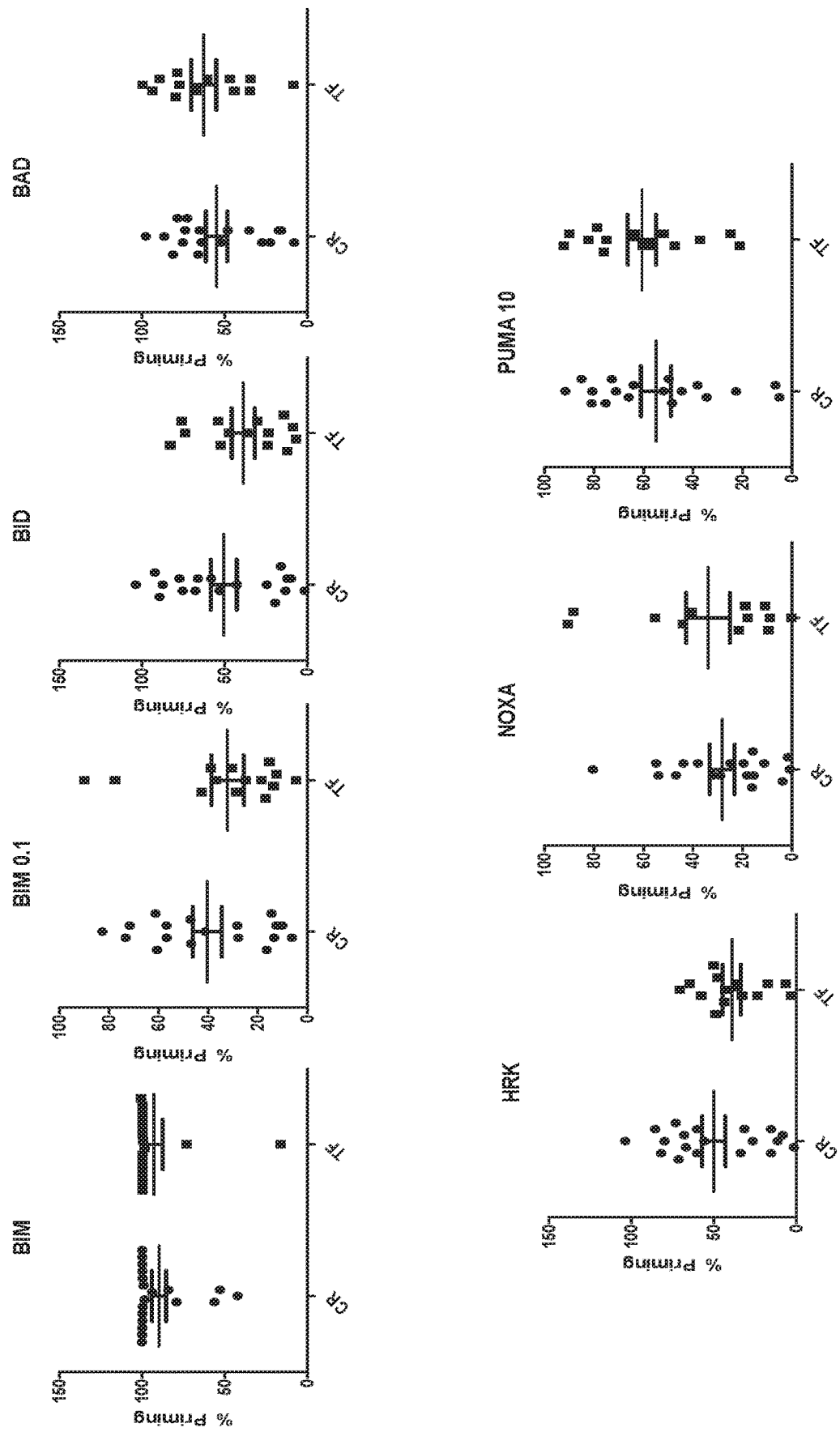
Figure 5C: Lack of correlation between assay readouts in peripheral blood samples and AML patient response Figure 7. CTD2 association alvocidib vs dinaciclib Figure 8: NOXA priming in azacitidine and decitabine responding cells Figure 9 Mcl-1 priming correlates to direct perturbation of Mcl-1 by BH3 mimetic compound. Cell lines shown to be primed by Noxa are also responsive to an Mcl-1 selective BH3 mimetic compound, EU5346 [Richard et al 2013].

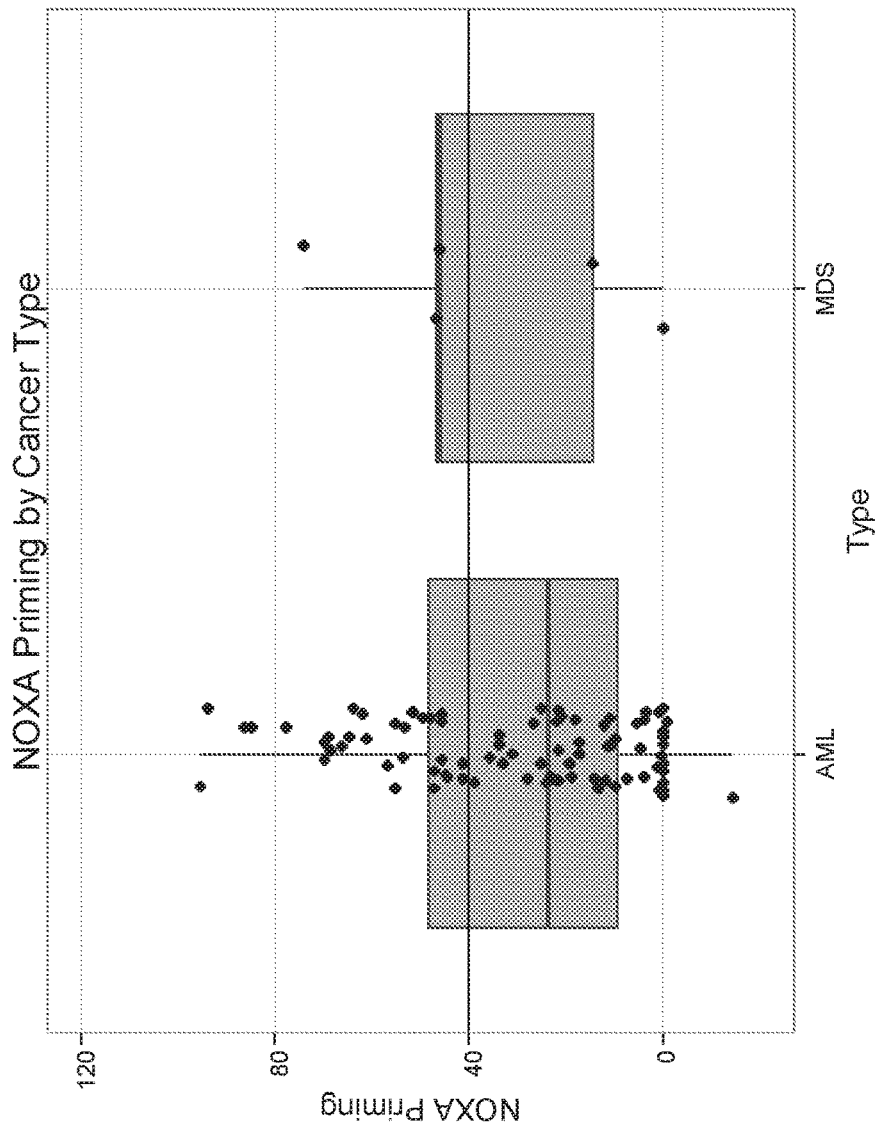
Figure 10A: Indication that Noxa priming is represented in the AML and MDS patient samples representing the patient population 60 years old or older. Noxa priming was assessed using the PraediCare Dx™ test, a FACS BH3 Profiling Assay

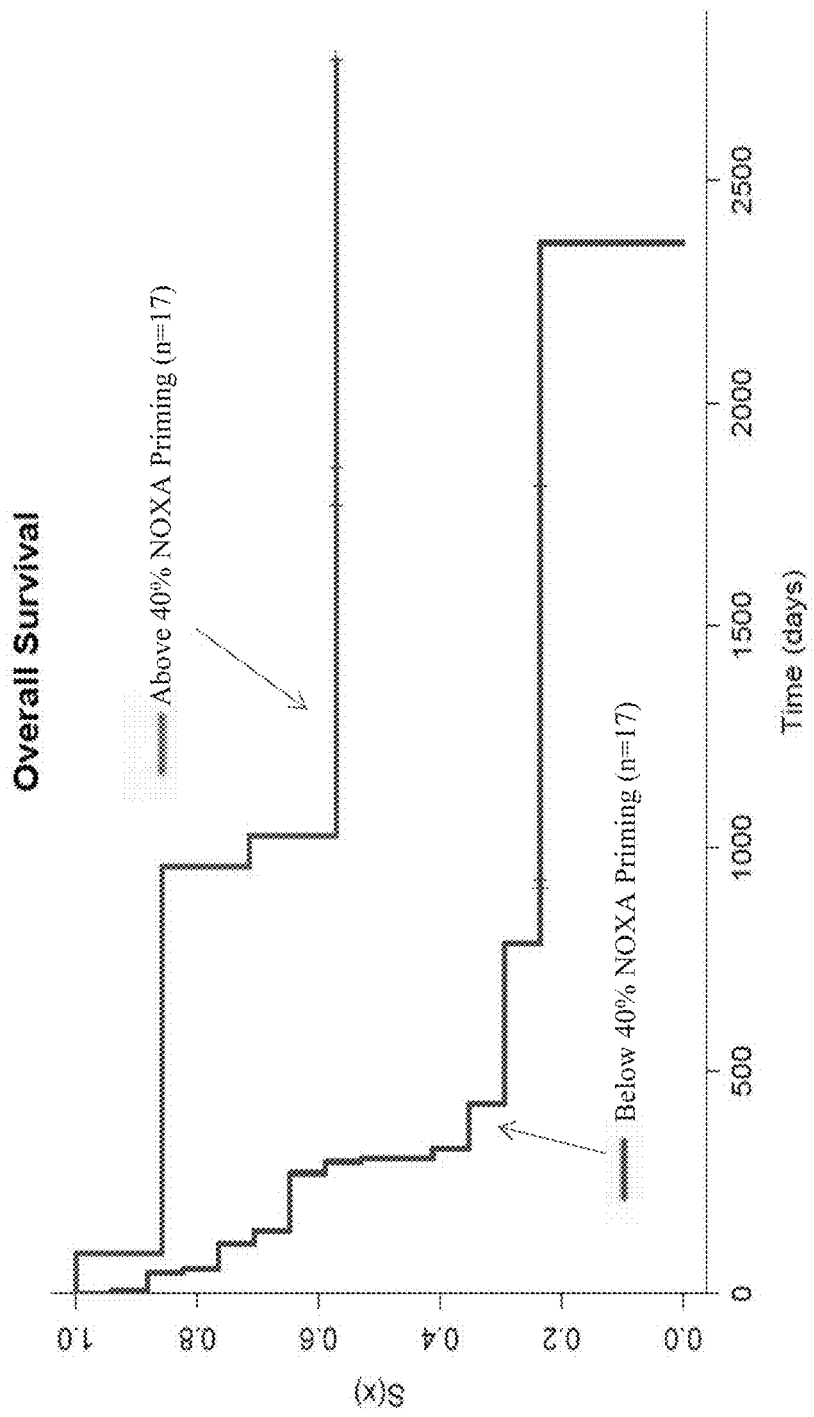
Figure 10B Noxa priming index showing patient survival on a FLAM regimen. S(x) is plotted against overall survival in AML patients treated with FLAM. The survival curve uses 40% as a cutoff.

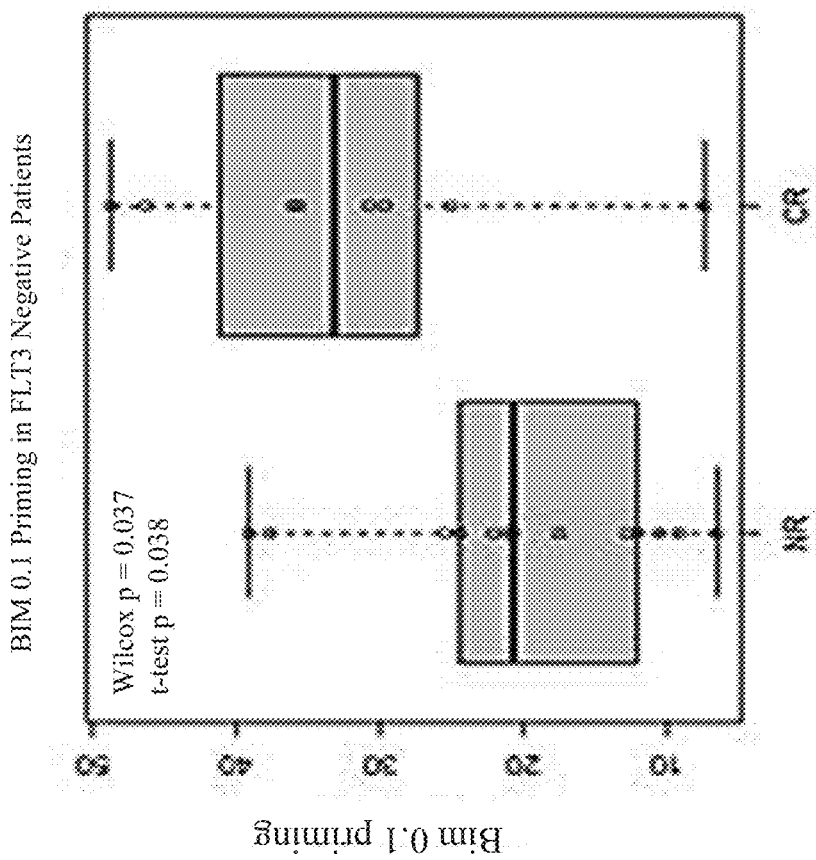
Figure 11A: Priming AML patient samples categorized by FLT3 mutational status.

CONTEXT DEPENDENT DIAGNOSTICS TEST FOR GUIDING CANCER TREATMENT

CROSS-REFERENCE TO RELATED APPLICATIONS

This application is the National Stage of International Application No. PCT/US2016/013003, filed Jan. 12, 2016, which claims the benefit of priority to U.S. Provisional Application No. 62/102,499, filed Jan. 12, 2015, the contents of each are herein incorporated by reference in their entireties. This application incorporates by reference the contents of the following references in their entirety: PCT/US13/40585, filed May 10, 2013, which claims priority to U.S. provisional applications Nos. 61/645,253, filed May 10, 2012, and 61/780,252 filed Mar. 13, 2013.

DESCRIPTION OF THE TEXT FILE SUBMITTED ELECTRONICALLY

The contents of the text file submitted electronically herewith are incorporated herein by reference in their entirety: a computer readable format copy of the sequence listing (filename: EUTR_017_01WO_SeqList_ST25.txt, date recorded: Jan. 11, 2016, file size 4 kilobytes).

FIELD OF THE INVENTION

The present disclosure provides methods that are useful in evaluating tumors in human samples.

BACKGROUND

The use of predictive and prognostic biomarkers paired with targeted cancer therapies may hold the key to reducing drug development time, improving drug efficacy, and guiding clinical decision making. While there are advances in cancer treatment, chemotherapy remains largely inefficient and ineffective. One reason for the generally poor performance of chemotherapy is that the selected treatment is often not closely matched to the individual patient's disease. A personalized medicine approach that couples precise diagnostics with therapeutics might alleviate this problem. In July of, 2014 the FDA issued "Guidance for Industry: In Vitro Companion Diagnostic Devices," to help companies identify the need for companion diagnostics at an earlier stage in the drug development To date there are only a handful of biomarkers that have added value to clinical oncology practice. In part this is because perceived markers often are correlative but not causal to drug mechanism. Even when the "biomarker" biology does line up with the pharmacology of the companion therapy, there is still significant challenge in predicting how a drug will work in each patient. Beyond this, the path to clinical development requires the participation of physician-scientists who see the value of the test and believe it can bring benefit to their patients.

The anti-apoptotic BCL-2 family proteins are pivotal causal factors to cancer cell response to chemotherapy. Measurements of the functionality of these proteins in modulating mitochondrial apoptosis has proven to provide predictive biomarkers for cancer patient response to treatment. Many chemotherapies rely on apoptosis to be effective and in some cases modulation of apoptosis by a specific anti-apoptotic proteins correlates with responsiveness to particular therapy. The measurement of a particular protein then provides the biomarker for drug response. Accordingly, biomarkers that determine the expected response to a therapeutic agent continue to be sought after.

SUMMARY OF THE INVENTION

Accordingly, in one aspect, the invention provides a method for selecting a cancer treatment for a patient, comprising measurement of response to agents that perturb the MCL1 and BFL1 proteins in their function to sequester pro-apoptotic proteins using BH3 profiling of patient cancer cells and inclusion of one or more clinical features of the patient into a predictive algorithm to classify each patient's likelihood of clinical response to one or more cancer treatments that perturb the function of MCL1.

In some embodiments, and as shown herein, patient cancer specimens are comprised of cancer cells purified from bone marrow aspirates. Cancer cells are exposed to agents that selectively perturb MCL1, or MCL1 and BFL1 binding to pro-apoptotic proteins BIM, Bid, Bax or Bak as determined using peptides comprising the BH3 only protein NOXA or BH3 mimetics that are selective for MCL1 or MCL1 and BFL1

In some aspects, the NOXA peptide used in the assay is AELPPEFAAQLRKIGDKVYC (SEQ ID NO:1). In other aspects, the NOXA peptide may comprise SEQ ID NO:1. In some aspects, SEQ ID NO:1 is used as a core NOXA peptide and the NOXA peptide may include flanking sequence from the endogenous NOXA protein. For example, in some aspects, the NOXA peptide may be MPGK-KARKNAQPSPARAP[AELPPEFAAQLRKIGDKVYC]FRQKLLNLISKLFCSGT (SEQ ID NO:2). In other aspects, the flanking sequence may include the core and up to 10 amino acids, up to 20 amino acids, up to 30 amino acids or up to 40 amino acids from the NOXA peptide extending from the region having identity to the core (i.e., AEL . . . KLN), as measure by BLAST against NP_066950 using default parameters. The amino acids may be added to the N-terminus, the C-terminus, or both. Amino acids may be numbered according to, and selected from, the sequence provided at Genbank entry NP_066950. In other aspects, the core peptide used is the wild-type sequence in having identity to the SEQ ID NO:1 peptide (i.e., AEL . . . KLN).

In addition to peptides based on variations in the length or homology to the NOXA sequence, peptides may also be modified to allow for increased cell penetration through bulk flow or clathrin-mediated endocytosis, for instance through fusions of the NOXA sequence with the TAT sequence (such as disclosed in Lin et al., "Therapeutic applications of the TAT-mediated protein transduction system for complex I deficiency and other mitochondrial diseases," Annals of the New York Academy of Sciences 1350, 17-28), peptides optimized for binding to MCL-1 through mutagenesis and selection for improved affinity (Dutta et al. "Determinants of BH3 binding specificity for Mcl-1 versus Bcl-xL. Journal of molecular biology" 398, 747-762 (2010)), and peptides modified by addition of chemical moieties to have improved stability of the alpha-helix (See structural and functional information in Stewart et al., "The MCL-1 BH3 helix is an exclusive MCL-1 inhibitor and apoptosis sensitizer," Nature chemical biology 6, 595-601, (2010)). Further, NOXA mimetic compounds that are identified through large scale functional binding screens, such as those defined in PCT/US2013/046826 (also published as U.S. Application Publication No. 2015-0150869) may be used as in place of the NOXA peptide as an additional or substituted marker of MCL-1 dependency in the NOXA priming assay. In addition suitable peptides to assess BH3 priming for additional BH3 proteins are disclosed in table 1 of PCT/US2013/046826 (also published as U.S. Application Publication No. 2015-0150869), which is incorporated by reference for those peptides.

In some embodiments, and as shown herein, BH3 assay readouts from patient cancer specimens comprised of cancer cells purified from bone marrow aspirates and BH3 profiling readouts from peripheral blood are compared. The different readouts predict response to distinct treatment options. Further, BH3 profiling conducted on AML cells taken from patient bone marrow has been shown to predict FLAM treatment whereas BH3 profiling on AML cells from peripheral blood does not, but does predict 7+3 treatment.

In some embodiments, and as shown herein, various clinical factors, even those unrelated or not known to be related to apoptosis, may be used to increase the predictive power of BH3 profiling, transforming the test to a predictive, not merely prognostic, test.

In some embodiments, the methods described herein provide a diagnostic test that is predictive of a leukemia patient response to a CDK-9 inhibiting compound. In some aspects, the CDK-9 inhibitor is Flavopiridol (alvocidib). In additional aspects, the CDK-9 inhibitor may be co-administered with one or more additional compounds as part of a therapeutic regimen. For example, a regimen may be alvocidib in combination with ara-C and mitoxantrone (FLAM). Additional variables may be considered to increase the sensitivity of the assay variables. For example, patient cytogenetic profile or status and/or age may be factored into a predictive algorithm. In some embodiments, the diagnostic test comprises measuring function of MCL1, including measuring change in mitochondrial membrane potential in response to the BH3 peptide NOXA, or the MCL1/Bfl-1 selective BH3 mimetic compounds EU5346 (compound 9 in D. Richard et al. Molecular Cancer Therapeutics, 2013).

In another aspect, the invention provides a method for determining a cancer treatment for a patient, comprising delivering one or more BH3 domain peptides to permeabilized patient cancer cells to determine the extent of priming; determining the presence or absence of one or more clinical factors of the patient's cancer cells by immunohistochemistry and/or fluorescent in situ hybridization (FISH); and classifying the patient for likelihood of clinical response to one or more cancer treatments.

In another aspect, the invention provides a method for determining an AML patient response to alvocidib or FLAM treatment comprising: determining a BH3 profile for the patient's AML cancer cell specimen collected from bone marrow; determining one or more clinical factors of the patient, and wherein the one or more clinical factors are selected from age profile and/or cytogenetic status; and classifying the patient for likelihood of clinical response to one or more cancer treatments.

In another aspect, the invention provides a method for determining an AML patient response to alvocidib or FLAM treatment, or cytarabine-based treatment alone comprising: determining a BH3 profile for the patient's AML cancer cell specimen collected from bone marrow; determining one or more clinical factors of the patient, and wherein the one or more clinical factors are selected from age profile and/or cytogenetic status; and classifying the patient for likelihood of clinical response to one or more cancer treatments. This readout is then compared to the BH3 profile readout from peripheral blood specimens. Specifically the BH3 profile readout of the BIM BH3 peptide at 0.1 μM has been demonstrated to be predictive for ara-C based treatment without alvocidib.

In another aspect, the invention provides a method for determining an AML patient response to an (interleukin-6) IL-6 antagonizing therapeutic or an MCL1 selective BH3 mimetic comprising: determining a BH3 profile for the patient's AML cancer cell specimen collected from bone marrow; determining one or more clinical factors of the patient, and wherein the one or more clinical factors are selected from age profile and/or cytogenetic status; and classifying the patient for likelihood of clinical response to one or more cancer treatments. This readout is then compared to the BH3 profile readout from peripheral blood specimens.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

Further, the in vivo context of the cancer cell affects the extent to which the MCL1 protein is involved in the onset and maintenance of the cancer, and the efficacy of MCL1 targeted therapies. Specifically, myeloid leukemia and myeloma cells that are in the stroma of the bone marrow are more dependent on MCL1 for survival than those that are circulating in the peripheral blood. Further, it has been established that BIM BH3 peptide from the peripheral blood samples correlates to AML patient response to ara-C with anthracycline, 7+3. Neither this readout; however, nor any BH3 profiling readout from the leukemia cells in the peripheral blood predicts AML patient response to FLAM or to other MCL1 inhibiting therapies.

While BH3 profiling, on its own, is known to provide a general indication of chemosensitivity or chemoresponsiveness to therapies. Here; however, recognizing the specific correlate for mechanisms that are focused on the MCL1 protein provides a uniquely sensitive method for predicting patient response to MCL1 affecting treatments. This; however, is only true for certain MCL1 targeting therapies when the cancer cells are isolated from the stroma of the bone marrow.

BRIEF DESCRIPTION OF THE FIGURES

FIG. 3A-C shows NOXA BH3 Peptide Association by dot blot correlation analysis with Response in bone marrow-derived FLAM treated patient specimens. NOXA priming alone shows predictive value in bone marrow stromal context samples. Panels A-C show dot plots representing NOXA priming measured in all samples (A), and those taken from the bone marrow (B) or the peripheral blood (C). Samples obtained from the bone marrow show a significant associate with CR, which is not seen in samples taken from the peripheral blood stromal context.

FIGS. 5A to 5C illustrate examples of priming for predicting response to treatment. FIG. 5A shows examples of BIM 0.1 (left panel) and NOXA (right panel) profiling. FIG. 5B shows a lack of correlation between assay readouts in mixed peripheral and bone marrow blood samples for certain individual BH3 peptides. FIG. 5C shows a lack of correlation between assay readouts in peripheral blood samples for AML patients.

FIGS. 10A and 10B illustrate a relationship between NOXA priming in AML patients on a FLAM regimen. FIG. 10A shows NOXA priming is represented in the AML and MDS patient samples representing the patient population 60 years old or older. NOXA priming as assessed using the Praedicare Dx test. FIG. 10B shows NOXA priming index, the survival function, $S(x)$, is plotted against time in AML patients treated with FLAM. The survival curve uses 40% NOXA priming as a cutoff. There were 7 complete remissions (CRs) in this group and 17 non-responders (NRs). The median survival of the NOXA low group was 303 days and median survival wasn't reached for the NOXA high group. Our 95% lower confidence bands are 142 days lower and undetermined upper for NOXA low and 959 days lower and undetermined upper for NOXA high. A log-rank test for survival differences between the NOXA high and low groups gives a p value of 0.023.

FIGS. 11A and 11B shows mitochondrial profiling association of 64 AML patient samples categorized by FLT3 mutational status, and categorized by response to decitabine. The pre-treatment sample priming was correlated with response to decitabine as a single agent (FIG. 11A). The FLT3 mutation negative patients who responded to decitabine treatment there was significantly higher mitochondrial response to BH3 mimetics, BIM 0.1 (p=0.04) compared with those who did not respond. Patients with FLT3 mutations had significantly (p=0.02) higher BIM 0.1 priming in general (FIG. 11B).

FIG. 12 illustrates the priming of BIM 0.1 and HRK (FIGS. 12A and 12B, respectively) in the FLT3 negative patients, where we see an association of higher priming with response to decitabine. This association was tested with rank sum tests and t-tests, and the results of which are shown in each plot. Bottom panel shows the association of BIM 0.1 (FIG. 12C) and HRK (FIG. 12D) priming with the FLT3 status of the patients, where FLT3 priming appears to be higher in the FLT3 ITD positive patients. This association was tested with linear regression analysis with priming as the response and FLT3 status as the predictor. The overall model p-values (by f-statistic) and the FLT3 ITD coefficient p-values (by t-statistic) are shown in each of the below plots. This suggests that FLT3-positive status is associated with higher priming than FLT3-negative patients.

Figure 1A:
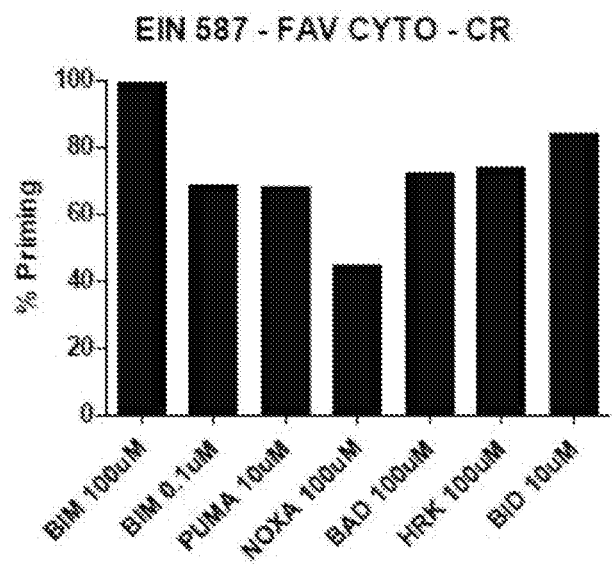
FIG. 1A-E shows representative BH3 profiling data from bone marrow samples obtained from patients that were treated with the FLAM regimen. The figure shows differences in patterns of high versus low primed blast cells from AML patients. The cutoff identified with the highest combined sensitivity and specificity by ROC analysis for NOXA priming in the bone marrow was approximately 10.7%, and a cutoff at 40% gives 100% positive predictive value (PPV) with a 70.5% negative predictive value (NPV). Varying this threshold for classification of patients as responders or non-responders will yield differing levels of sensitivity and specificity, and the choice of that threshold will depend on the nature of the investigation. For instance, if the goal is to identify every patient that will respond to an agent, a lower threshold will be chosen at the expense of producing false positive results, or if the goal is to identify positive with the highest accuracy (PPV), then a higher threshold may be chosen for a given study. Therefore, classification based on NOXA priming is not absolute and can be adjusted to accommodate the desired medical utility. Panels A-C show examples of each cytogenetic risk category context (Fav-favorable, adv-adverse, and int-intermediate) showing patients with high NOXA priming that underwent CR. Panels D-E show an intermediate risk and adverse risk patients with low NOXA priming that had treatment failures.
Figure 1B:
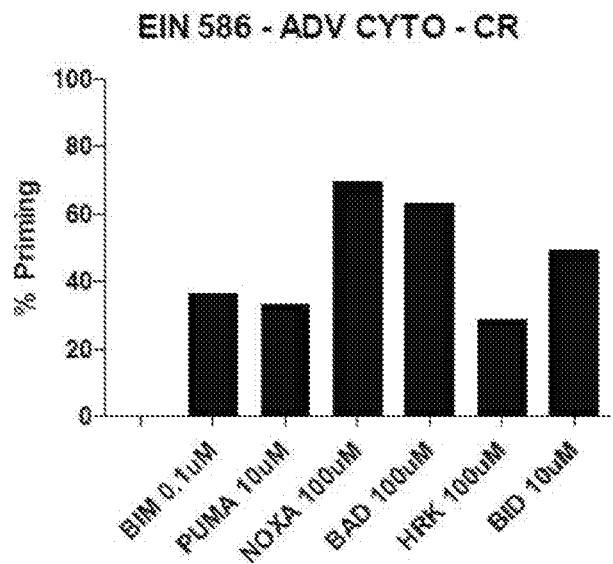
Figure 1C:
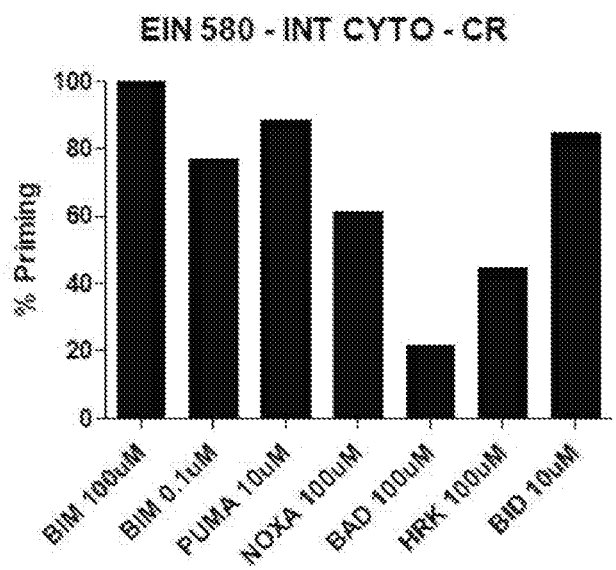
Figure 1D:
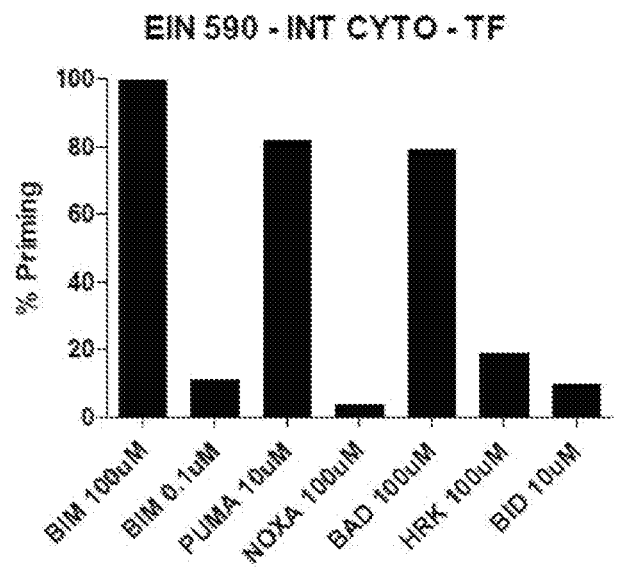
Figure 1E:
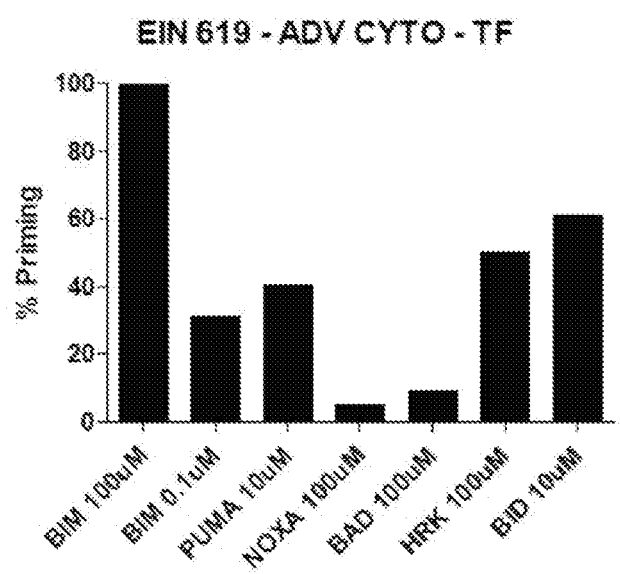
Figure 2A:
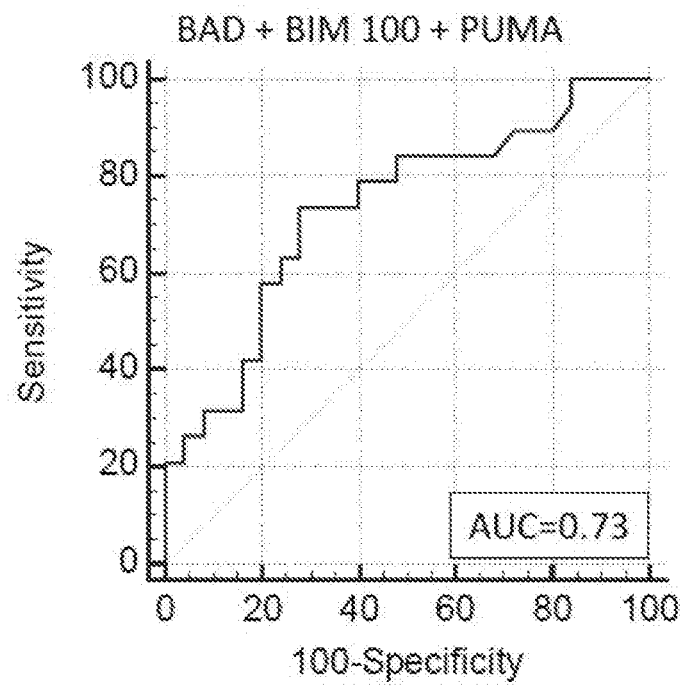
FIG. 2A-F shows BH3 Peptide Association with response to FLAM by receiver operating characteristic (ROC) curve analyses in all FLAM-treated patient specimens. Panels A, C, and E show the receiver operating characteristic (ROC) curve analyses of BAD, BIM 100, and PUMA in combination with the cytogenetic risk factor and MDS (Myelodysplastic Syndromes) history clinical variables. Panels B, D, and F show corresponding dot plots illustrating each patient data point from the combined metrics in the patients who reached CR compared with those who did not.
Figure 2B:
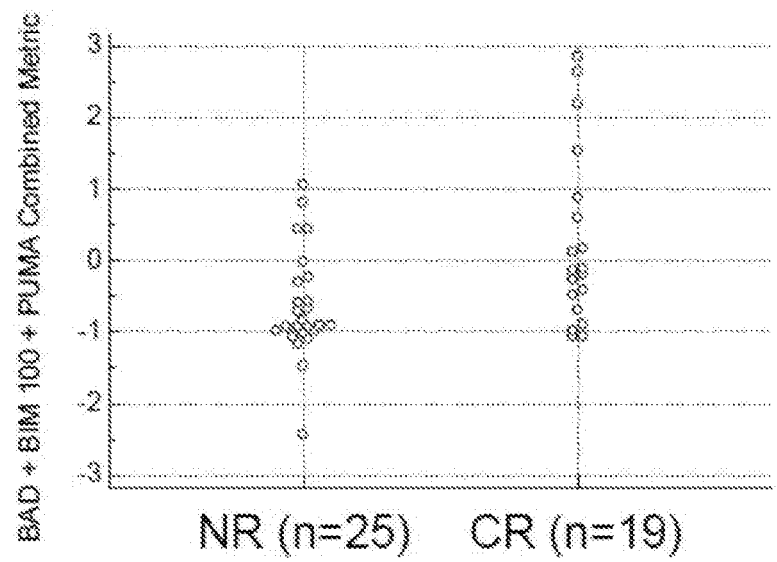
Figure 2C:
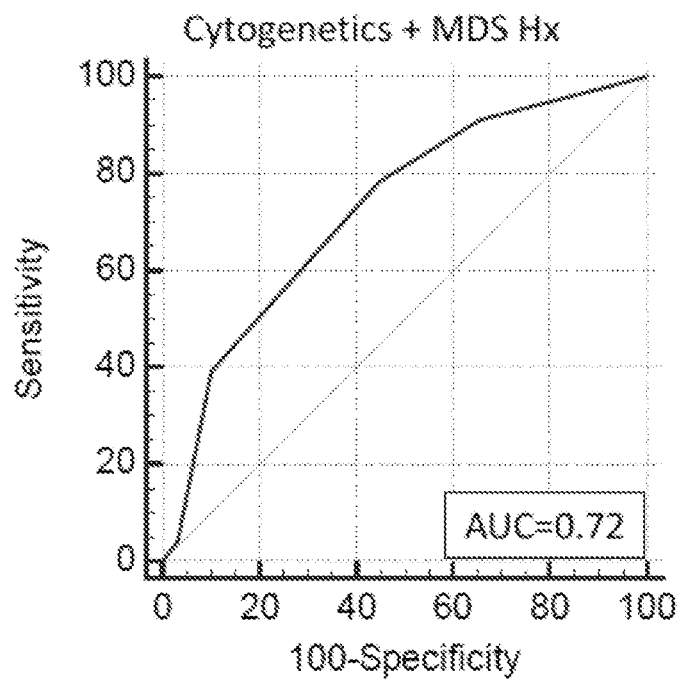
Figure 2D:
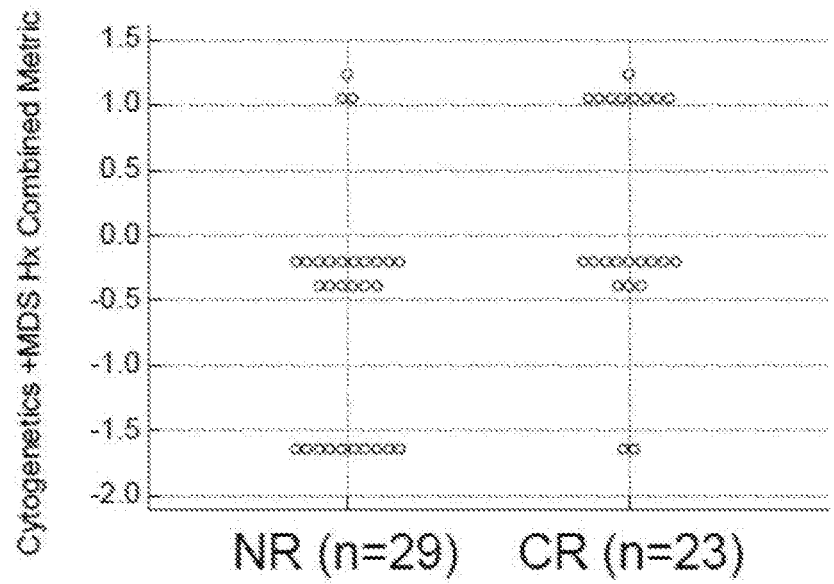
Figure 2E:
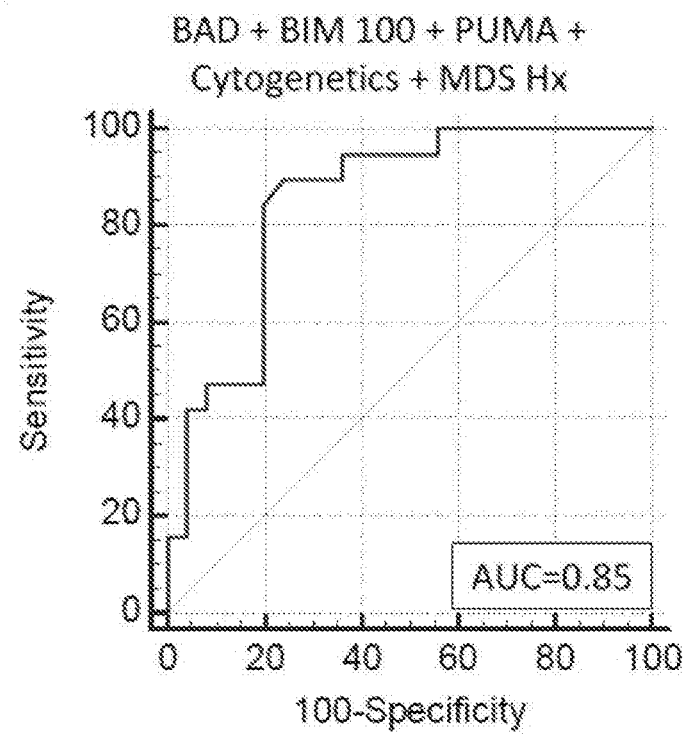
Figure 2F:
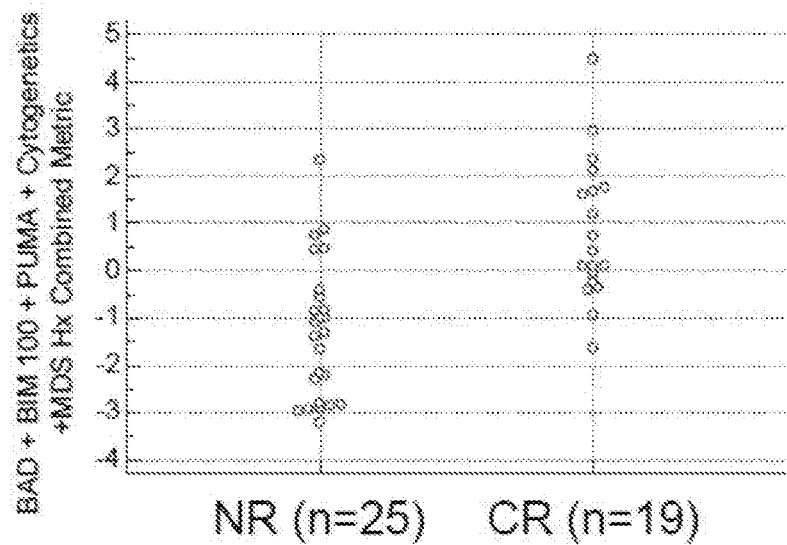
Figure 4:
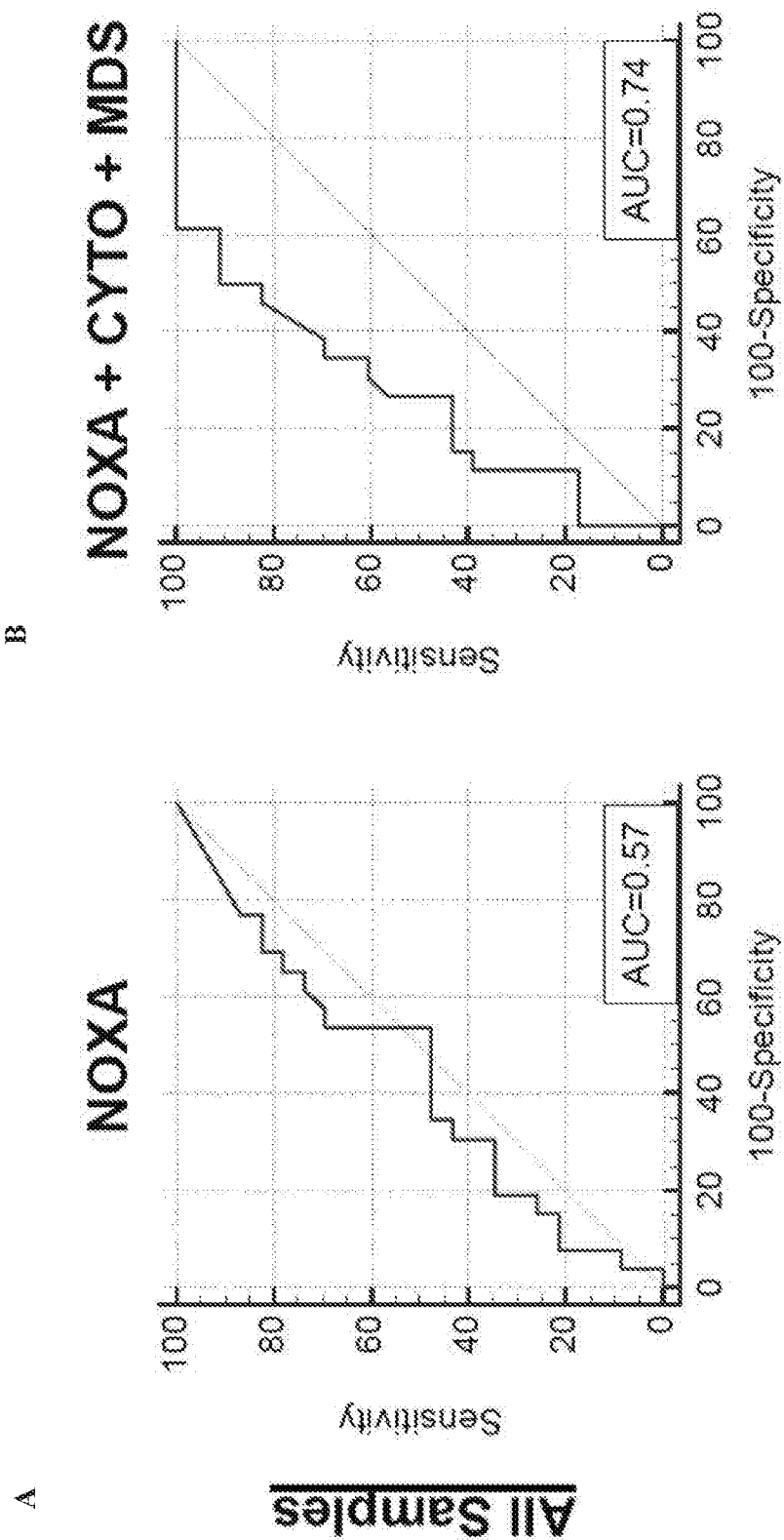
FIG. 4A-D shows NOXA BH3 Peptide association with response by receiver operating characteristic (ROC) curve analyses in bone marrow-derived contextual FLAM treated patient specimens. Figs A and B show the receiver operating characteristic (ROC) curve analyses of NOXA peptide priming in combination with the cytogenetic risk factor and MDS history clinical variables in all samples. Figs C and D show the same in samples drawn from bone marrow, but not in samples from the peripheral blood. Addition of cytogenetic risk factor and MDS history improves the predictive power of the test, with an AUC value of 0.92 in BM NOXA priming with cytogenetic risk factor and MDS history.
Figure 4:
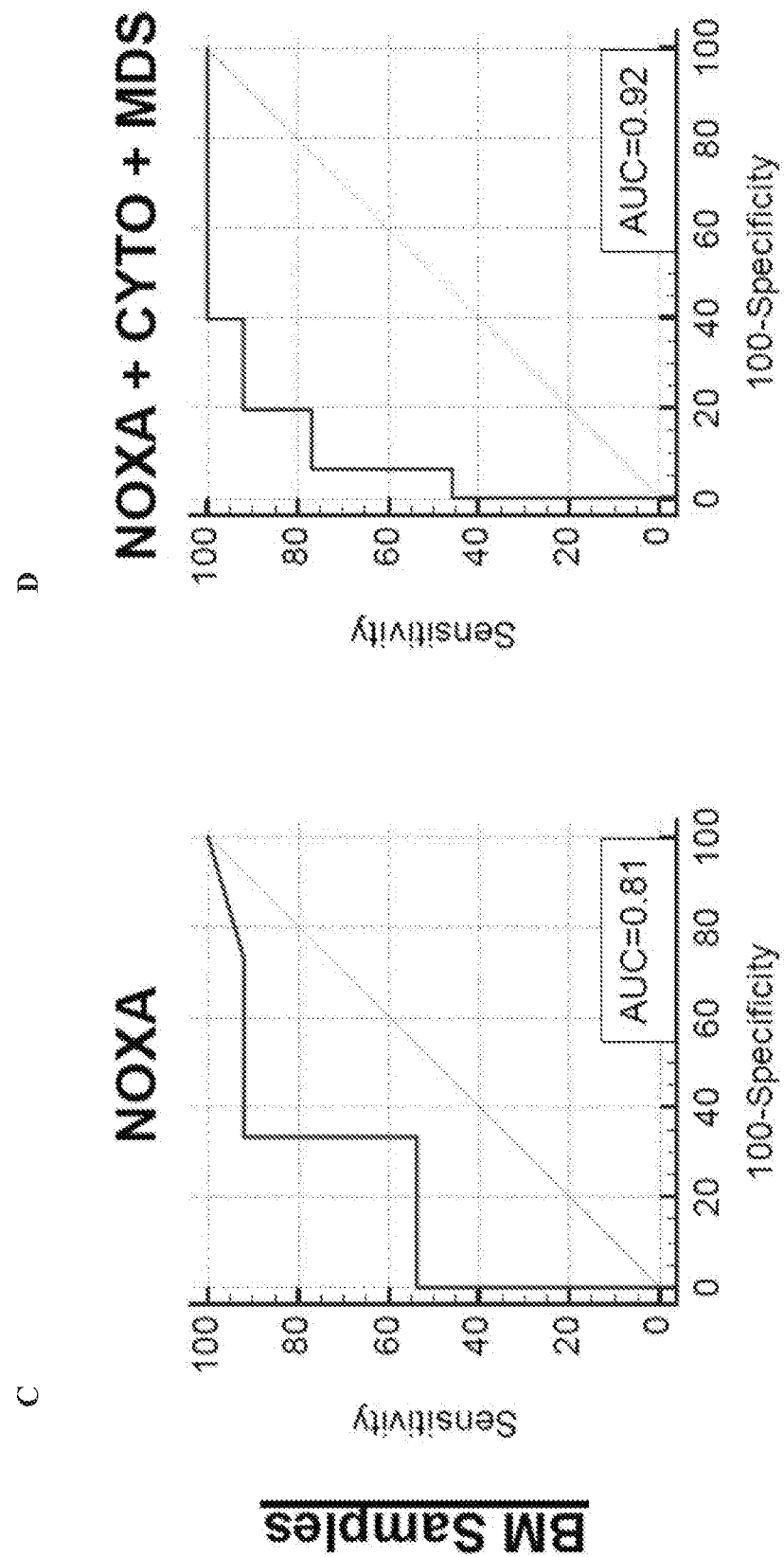

Table 1 shows a FLAM patient study. The overall patient summary is shown in the table, with the numbers of patients positive in each context over the total number with available data for each value.

Table 2 shows FLAM treated patient summary analysis. The table lists all samples obtained. Patients were enrolled on three different protocols (J0669, J0856, and J01101) and were mostly newly diagnosed AML patients. Samples were obtained from either the peripheral blood or bone marrow aspirates. Age was calculated at the time of diagnosis. Cytogenetic risk factor was determined using CALGB guidelines. Cytogenetics, FLT-3, and NPM1 mutations status, MDS history, chemotherapy history, percent bone marrow blast, white blood cell (WBC) counts, treatments, and response were all obtained. Samples that are shaded gray (EIN 576, 578, 579, 581, 600, 609, 611, 613, 617, 618, and 623) were not successfully assayed for BH3 priming and are excluded from all subsequent analyses (MRD—minimal residual disease, TF—treatment failure, PR—partial response, CR—complete remission). Complete response (CR) is characterized by one or more, typically all, of the following: less than 5% myeloblasts with normal maturation of all cell lines, an ANC≥1000/µL and platelet count ≥100,000/µL, absence of blast in peripheral blood, absence of leukemic cells in the marrow, clearance of cytogenetics associated with disease, and clearance of previous extramedullary disease.

Table 3 shows the Clinical Characteristics Associations with FLAM Response. Statistical analyses of clinical variables were performed relative to response. Each of the indicated metrics was tested for significance by the rank-sum Mann-Whitney test and by Logistic Regression analysis. The AUC (area under the curve) was obtained from ROC curve analysis.

Table 4 shows the BH3 Profiling Data from FLAM patient study. BH3 profiling was performed on all patient samples listed in Table 2. Rows that are shaded grey are samples that failed the acceptance criteria of BH3 profiling during processing. Any cell containing a dash (-) did not have sufficient cells to perform the respective BH3 peptide assay for the indicated sample. Signal to noise is a measure of the DMSO JC-1 red mean fluorescence intensity (MFI) over the CCCP JC-1 read MFI. The cell counts and percent viability were determined by manual cell counting with trypan blue exclusion. Percent blasts are the percentages of CD45-dim, CD3/CD20 negative, and SSC-low of the permeabilized viable cells. All BH3 profiling was performed on those gated blast cells.

Table 5 shows Associations of individual BH3 peptide profiles with CR. Statistical analyses of BH peptides were performed relative to response, with CR samples compared with all partial responses, minimal residual diseases, and treatment failures (NR-non-responder). Each of the indicate metrics was tested for significance by the rank-sum Mann-Whitney test and by Logistic Regression analysis. The AUC (area under the curve) was obtained from ROC curve analysis.

Table 6 shows Multivariate Analysis of BH3 Peptide Profiling with Other Clinical Variables in FLAM study. Statistical analyses of BH3 peptides were performed relative to response, with CR samples compared with NR samples. Combinations of variables were tested using logistic regression to determine coefficients and constants under a logistic regression model, and then these coefficients and constants were tested by the rank-sum Mann-Whitney test and ROC curve analysis.

Table 7 shows Associations of Individual BH3 Peptide Profiles with CR in Bone Marrow Samples. Statistical analyses of BH3 peptides were performed in only those samples that were obtained from bone marrow as done in Table 5. Each of the indicated metrics was tested for significance by the rank-sum Mann-Whitney test and by Logistic Regression analysis. The AUC (area under the curve) was obtained from ROC curve analysis. This analysis reveals that NOXA priming is significantly higher in the patients that responded to treatment compared with the non-responders.

Table 8 shows statistical analyses of BH3 peptides in samples from the bone marrow stromal context. Mann-Whitney p-values were determined using the priming values or calculated log-likelihoods from logistic regression. Logistic regression p-values were calculated through ANOVA analysis of the final model versus the null model. This analysis shows that the combination of BAD, BIM 100, and PUMA is also associated with response in bone marrow samples alone. Both the NOXA and the three peptide readouts are additive to the cytogenetic risk category and MDS history and result in higher significance and AUC values.

DETAILED DESCRIPTION OF THE INVENTION

The present disclosure is based, in part, on the discovery that the medical utility of the BH3 profiling assay can be realized for predicting response to CDK inhibitors, such as a CDK-9 inhibitor (e.g. alvocidib) alone or in a co-treatment regime (e.g., FLAM) by measuring the response in cancer cells that have been from patient bone marrow stroma. The sensitivity and/or specificity of BH3 profiling measurements are significantly improved over blood collected from peripheral blood or combinations of peripheral blood samples and bone marrow samples. It was seen that a dramatic increase in association of the NOXA generated signal with response, as shown by a p-value decrease from 0.445 to 0.0007 when using only the samples from the bone marrow stromal context. (Tables 6 and 7). The sensitivity of the assay improved from 0.805 (AUC) to 0.91 (AUC) when clinical variables, cytogenetics, and age contexts were factored into the analysis. Different algorithms are provided herein to predict response of AML patients to FLAM treatment. In one aspect, NOXA priming is used alone to predict patient response to a FLAM regimen. In another aspect, BAD+BIM 100+PUMA priming may be used in combination to predict patient response to a FLAM regimen. The diagnostic approaches described herein provide a new method for predicting response to MCL1 perturbing therapies.

In one aspect, the invention provides a method for determining a cancer treatment for a patient, comprising determining the extent of MCL1 dependence in a patient's tumor or cancer cell specimen from bone marrow; determining one or more clinical factors of the patient, and classifying the patient for likelihood of clinical response to one or more cancer treatments; wherein one or more clinical factors are selected to increase specificity and/or sensitivity of the MCL1 specific BH3 profiling readout for association with clinical response.

In another aspect, the invention provides a method for determining a cancer treatment for a patient, comprising exposing permeabilized cancer cells of the patient to the NOXA BH3 domain peptides to determine the extent of priming; determining the presence or absence of one or more clinical factors of the patient's cancer cells by immunohistochemistry and/or fluorescent in situ hybridization (FISH); and classifying the patient for likelihood of clinical response to one or more cancer treatments.

In another aspect, the invention provides a method for determining an AML patient response to cytarabine and/or FLAM comprising: determining a BH3 profile for the patient's AML cancer cell specimen taken from bone marrow or peripheral blood; comparing readouts from those two cancer cell sources and using that information to guide either FLAM or cytarabine based treatment.

In various embodiments, the clinical context is one or more of age, cytogenetic status, performance, histological subclass, gender, and disease stage. In another embodiment, the method further comprises a measurement of an additional biomarker selected from mutational status, single nucleotide polymorphisms, steady state protein levels, and dynamic protein levels, which can add further specificity and/or sensitivity to the test. In another embodiment, the method further comprises predicting a clinical response in the patient. In another embodiment, the clinical response is at least about 1, about 2, about 3, or about 5 year progression/event-free survival.

In certain embodiments, the priming is defined by the following equation:
in which the AUC comprises either area under the curve or signal intensity; the DMSO comprises the baseline negative control; and the CCCP (Carbonyl cyanide m-chlorophenyl hydrazone) comprises an effector of protein synthesis by serving as uncoupling agent of the $$\% \text{ Priming} = \left[100 * \frac{DMSO\ AUC - Peptide_1 AUC}{DMSO\ AUC - CCCP_{avg} AUC}\right] Peptide_1 +$$
$$\left[100 * \left(\frac{DMSO\ AUC - Peptide_2 AUC}{DMSO\ AUC - CCCP_{avg} AUC}\right)\right] Peptide_2 + \ldots /(n\ \text{peptides})$$

proton gradient established during the normal activity of electron carriers in the electron transport chain in the mitochondria comprises the baseline positive control. In some embodiments, the area under the curve is established by homogenous time-resolved fluorescence (HTRF). In some embodiments, the time occurs over a window from between about 0 to about 300 min to about 0 to about 30 min. In some embodiments, the area under the curve is established by fluorescence activated cell sorting (FACS) by the median fluorescence intensity (MFI) statistic. In some embodiments, the signal intensity is a single time point measurement that occurs between about 5 min and about 300 min. For an individual peptide, priming may be calculated as:

$$\text{Percentage Priming} = \left[1 - \frac{(Peptide - CCCP)}{(DMSO - CCCP)}\right] \times 100.$$

Exemplary Clinical Decisions

In some embodiments, the methods described herein are useful in the evaluation of a patient, for example, for evaluating diagnosis, prognosis, and response to treatment. In various aspects, the present invention comprises evaluating a tumor or hematological cancer. In various embodiments, the evaluation may be selected from diagnosis, prognosis, and response to treatment.

Diagnosis refers to the process of attempting to determine or identify a possible disease or disorder, such as, for example, cancer. Prognosis refers to predicting a likely outcome of a disease or disorder, such as, for example, cancer. A complete prognosis often includes the expected duration, the function, and a description of the course of the disease, such as progressive decline, intermittent crisis, or sudden, unpredictable crisis. Response to treatment is a prediction of a patient's medical outcome when receiving a treatment. Responses to treatment can be, by way of non-limiting example, pathological complete response, survival, progression free survival, time to progression, and probability of recurrence.

In various embodiments, the present methods direct a clinical decision regarding whether a patient is to receive a specific treatment. In one embodiment, the present methods are predictive of a positive response to neoadjuvant and/or adjuvant chemotherapy or a non-responsiveness to neoadjuvant and/or adjuvant chemotherapy. In one embodiment, the present methods are predictive of a positive response to a pro-apoptotic agent or an agent that operates via apoptosis and/or an agent that does not operate via apoptosis or a non-responsiveness to apoptotic effector agent and/or an agent that does not operate via apoptosis. In various embodiments, the present invention directs the treatment of a cancer patient, including, for example, what type of treatment should be administered or withheld.

In one embodiment, the present methods direct a clinical decision regarding whether a patient is to receive adjuvant therapy after primary, main or initial treatment, including, without limitation, a single sole adjuvant therapy. Adjuvant therapy, also called adjuvant care, is treatment that is given in addition to the primary, main or initial treatment. By way of non-limiting example, adjuvant therapy may be an additional treatment usually given after surgery where all detectable disease has been removed, but where there remains a statistical risk of relapse due to occult disease.

In some embodiments, the present methods direct a patient's treatment to include adjuvant therapy. For example, a patient that is scored to be responsive to a specific treatment may receive such treatment as adjuvant therapy. Further, the present methods may direct the identity of an adjuvant therapy, by way of non-limiting example, as a treatment that induces and/or operates in a pro-apoptotic manner or one that does not. In one embodiment, the present methods may indicate that a patient will not be or will be less responsive to a specific treatment and therefore such a patient may not receive such treatment as adjuvant therapy. Accordingly, in some embodiments, the present methods provide for providing or withholding adjuvant therapy according to a patient's likely response. In this way, a patient's quality of life, and the cost of care, may be improved.

In some embodiments, the present methods direct a clinical decision regarding whether a patient is to receive a specific type of treatment. Accordingly, in some embodiments, the present methods are a guiding test for patient treatment.

In some embodiments, the present methods provide information about the likely response that a patient is to have to a particular treatment. In some embodiments, the present methods provide a high likelihood of response and may direct treatment, including aggressive treatment. In some embodiments, the present methods provide a low likelihood of response and may direct cessation of treatment, including aggressive treatment, and the use of palliative care, to avoid unnecessary toxicity from ineffective chemotherapies for a better quality of life.

In an exemplary embodiment, the present method will indicate a likelihood of response to a specific treatment. For example, in some embodiments, the present methods indicate a high or low likelihood of response to a pro-apoptotic agent and/or an agent that operates via apoptosis and/or an agent that operates via apoptosis driven by direct protein modulation. In various embodiments, exemplary pro-apoptotic agents and/or agents that operate via apoptosis and/or an agent that operates via apoptosis driven by direct protein modulation include ABT-263 (Navitoclax), obatoclax, WEP, bortezomib, and carfilzomib. In some embodiments, the present methods indicate a high or low likelihood of response to an agent that does not operate via apoptosis and/or an agent that does not operate via apoptosis driven by direct protein modulation. In various embodiments, exemplary agents that do not operate via apoptosis include kinesin spindle protein inhibitors, cyclin-dependent kinase inhibitor, Arsenic Trioxide (TRISENOX), MEK inhibitors, pomolidomide, azacitidine, decitabine, vorinostat, entinostat, dinaciclib, gemtuzumab, BTK inhibitors, including ibrutinib, PI3 kinase delta inhibitors, lenolidimide, anthracyclines, cytarabine, melphalam, Akt inhibitors, mTOR inhibitors.

In an exemplary embodiment, the present method will indicate whether a patient is to receive a pro-apoptotic agent or an agent that operates via apoptosis for cancer treatment. In another exemplary embodiment, the present method will indicate whether a patient is to receive an agent that does not operate via apoptosis.

In a specific embodiment, the present methods are useful in predicting a cancer patient's response to any of the treatments (including agents) described herein. In an exemplary embodiment, the present invention predicts an AML patient's likelihood of response to cytarabine and azacitidine and comprises an evaluation of the BH3 profile, age profile and cytogenetic factors of the patient.

In various embodiments, a cancer treatment is administered or withheld based on the methods described herein. Exemplary treatments include surgical resection, radiation therapy (including the use of the compounds as described herein as, or in combination with, radiosensitizing agents), chemotherapy, pharmacodynamic therapy, targeted therapy, immunotherapy, and supportive therapy (e.g., painkillers, diuretics, antidiuretics, antivirals, antibiotics, nutritional supplements, anemia therapeutics, blood clotting therapeutics, bone therapeutics, and psychiatric and psychological therapeutics).

Exemplary Treatments

In exemplary embodiments, the invention calculates an expected response rate to specific treatment agents. Examples of such agents include, but are not limited to, one or more of anti-cancer drugs, chemotherapy, surgery, adjuvant therapy, and neoadjuvant therapy. In one embodiment, the cancer treatment is one or more of a BH3 mimetic, epigenetic modifying agent, topoisomerase inhibitor, cyclin-dependent kinase inhibitor, and kinesin-spindle protein stabilizing agent. In another embodiment, the cancer treatment is a proteasome inhibitor; and/or a modulator of cell cycle regulation (by way of non-limiting example, a cyclin dependent kinase inhibitor); and/or a modulator of cellular epigenetic mechanistic (by way of non-limiting example, one or more of a histone deacetylase (HDAC) (e.g. one or more of vorinostat or entinostat), azacitidine, decitabine); and/or an anthracycline or anthracenedione (by way of non-limiting example, one or more of epirubicin, doxorubicin, mitoxantrone, daunorubicin, idarubicin); and/or a platinum-based therapeutic (by way of non-limiting example, one or more of carboplatin, cisplatin, and oxaliplatin); cytarabine or a cytarabine-based chemotherapy; a BH3 mimetic (by way of non-limiting example, one or more of BCL2, BCLXL, or MCL1); and an inhibitor of MCL1.

In various embodiments, the invention pertains to cancer treatments including, without limitation, those described in US Patent Publication No. US 2012-0225851 and International Patent Publication No. WO 2012/122370, the contents of which are hereby incorporated by reference in their entireties.

In various embodiments, the invention pertains to cancer treatments including, without limitation, one or more of alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2', 2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111.), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-$\alpha$, Raf, H-Ras, EGFR (e.g., erlotinib (Tarceva)) and VEGF-A that reduce cell proliferation, dacogen, velcade, and pharmaceutically acceptable salts, acids or derivatives of any of the above.

Exemplary Detection Methods

In various embodiments, the present methods comprise evaluating a presence, absence, or level of a protein and/or a nucleic acid. In various embodiments, the present methods comprise evaluating a presence, absence, or level of a protein and/or a nucleic acid which can enhance the specificity and/or sensitivity of BH3 profiling. In some embodiments, the evaluation involves a marker for patient response. In some embodiments, the present methods comprise measurement using one or more of immunohistochemical staining, western blotting, in-cell western, immunofluorescent staining, ELISA, and fluorescent activating cell sorting (FACS), or any other method described herein or known in the art. The present methods may comprise contacting an antibody with a tumor specimen (e.g. biopsy or tissue or body fluid) to identify an epitope that is specific to the tissue or body fluid and that is indicative of a state of a cancer.

There are generally two strategies used for detection of epitopes on antigens in body fluids or tissues, direct methods and indirect methods. The direct method comprises a one-step staining, and may involve a labeled antibody (e.g. FITC conjugated antiserum) reacting directly with the antigen in a body fluid or tissue sample. The indirect method comprises an unlabeled primary antibody that reacts with the body fluid or tissue antigen, and a labeled secondary antibody that reacts with the primary antibody. Labels can include radioactive labels, fluorescent labels, hapten labels such as, biotin, or an enzyme such as horse radish peroxidase or alkaline phosphatase. Methods of conducting these assays are well known in the art. See, e.g., Harlow et al. (Antibodies, Cold Spring Harbor Laboratory, N Y, 1988), Harlow et al. (Using Antibodies, A Laboratory Manual, Cold Spring Harbor Laboratory, N Y, 1999), Virella (Medical Immunology, 6th edition, Informa HealthCare, New York, 2007), and Diamandis et al. (Immunoassays, Academic Press, Inc., New York, 1996). Kits for conducting these assays are commercially available from, for example, Clontech Laboratories, LLC. (Mountain View, Calif.).

In various embodiments, antibodies include whole antibodies and/or any antigen binding fragment (e.g., an antigen-binding portion) and/or single chains of these (e.g. an antibody comprising at least two heavy (H) chains and two light (L) chains inter-connected by disulfide bonds, an Fab fragment, a monovalent fragment consisting of the $V_L$, $V_H$, $C_L$ and CH1 domains; a F(ab)$_2$ fragment, a bivalent fragment including two Fab fragments linked by a disulfide bridge at the hinge region; a Fd fragment consisting of the $V_H$ and CH1 domains; a Fv fragment consisting of the $V_L$ and $V_H$ domains of a single arm of an antibody; and the like). In various embodiments, polyclonal and monoclonal antibodies are useful, as are isolated human or humanized antibodies, or functional fragments thereof.

Standard assays to evaluate the binding ability of the antibodies toward the target of various species are known in the art, including for example, ELISAs, western blots and RIAs. The binding kinetics (e.g., binding affinity) of antibodies also can be assessed by standard assays known in the art, such as by Biacore analysis.

In another embodiment, the measurement comprises evaluating a presence, absence, or level of a nucleic acid. A person skilled in the art will appreciate that a number of methods can be used to detect or quantify the DNA/RNA levels of appropriate markers.

Gene expression can be measured using, for example, low-to-mid-plex techniques, including but not limited to reporter gene assays, northern blot, fluorescent in situ hybridization (FISH), and reverse transcription PCR (RT-PCR). Gene expression can also be measured using, for example, higher-plex techniques, including but not limited, serial analysis of gene expression (SAGE), DNA microarrays. Tiling array, RNA-Seq/whole transcriptome shotgun sequencing (WTSS), high-throughput sequencing, multiplex PCR, multiplex ligation-dependent probe amplification (MLPA), DNA sequencing by ligation, and Luminex/XMAP. A person skilled in the art will appreciate that a number of methods can be used to detect or quantify the level of RNA products of the biomarkers within a sample; including arrays, such as microarrays, RT-PCR (including quantitative PCR), nuclease protection assays and northern blot analyses.

Exemplary Cancers and Patients

In some embodiments, the invention provides a method for determining a cancer treatment and/or comprises a patient's tumor or cancer cell specimen. A cancer or tumor refers to an uncontrolled growth of cells and/or abnormal increased cell survival and/or inhibition of apoptosis which interferes with the normal functioning of the bodily organs and systems. A subject that has a cancer or a tumor is a subject having objectively measurable cancer cells present in the subject's body. Included in this invention are benign and malignant cancers, as well as dormant tumors or micrometastases. Cancers which migrate from their original location and seed vital organs can eventually lead to the death of the subject through the functional deterioration of the affected organs.

In various embodiments, the invention is applicable to pre-metastatic cancer, or metastatic cancer. Metastasis refers to the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant. Metastases are often detected through the sole or combined use of magnetic resonance imaging (MRI) scans, computed tomography (CT) scans, blood and platelet counts, liver function studies, chest X-rays and bone scans in addition to the monitoring of specific symptoms.

The methods described herein are directed toward the prognosis of cancer, diagnosis of cancer, treatment of cancer, and/or the diagnosis, prognosis, treatment, prevention or amelioration of growth, progression, and/or metastases of malignancies and proliferative disorders associated with increased cell survival, or the inhibition of apoptosis. In some embodiments, the cancer is a hematologic cancer, including, but not limited to, acute myelogenous leukemia (AML), multiple myeloma, follicular lymphoma, acute lymphoblastic leukemia (ALL), chronic lymphocytic leukemia, and non-Hodgkin's lymphoma including, but not limited to, mantle cell lymphoma and diffuse large B-cell lymphoma. In some embodiments, the cancer is a solid tumor, including, but not limited to, non-small lung cell carcinoma, ovarian cancer, and melanoma.

In some embodiments, the invention relates to one or more of the following cancers: acute lymphoblastic leukemia (ALL), acute myeloid leukemia (AML), adrenocortical carcinoma, AIDS-related cancers, anal cancer, appendix cancer, astrocytoma (e.g. childhood cerebellar or cerebral), basal-cell carcinoma, bile duct cancer, bladder cancer, bone tumor (e.g. osteosarcoma, malignant fibrous histiocytoma), brainstem glioma, brain cancer, brain tumors (e.g. cerebellar astrocytoma, cerebral astrocytoma/malignant glioma, ependymoma, medulloblastoma, supratentorial primitive neuroectodermal tumors, visual pathway and hypothalamic glioma), breast cancer, bronchial adenomas/carcinoids, Burkitt's lymphoma, carcinoid tumors, central nervous system lymphomas, cerebellar astrocytoma, cervical cancer, chronic lymphocytic leukemia (CLL), chronic myelogenous leukemia (CML), chronic myeloproliferative disorders, colon cancer, cutaneous T-cell lymphoma, desmoplastic small round cell tumor, endometrial cancer, ependymoma, esophageal cancer, Ewing's sarcoma, extracranial germ cell tumor, extragonadal germ cell tumor, extrahepatic bile duct cancer, eye cancer, gallbladder cancer, gastric (stomach) cancer, gastrointestinal stromal tumor (GIST), germ cell tumor (e.g. extracranial, extragonadal, ovarian), gestational trophoblastic tumor, gliomas (e.g. brain stem, cerebral astrocytoma, visual pathway and hypothalamic), gastric carcinoid, head and neck cancer, heart cancer, hepatocellular (liver) cancer, hypopharyngeal cancer, hypothalamic and visual pathway glioma, intraocular melanoma, islet cell carcinoma (endocrine pancreas), kidney cancer (renal cell cancer), laryngeal cancer, leukemias (e.g. acute lymphocytic leukemia, acute myelogenous leukemia, chronic lymphocytic leukemia, chronic myeloid leukemia, hairy cell), lip and oral cavity cancer, liposarcoma, liver cancer, lung cancer (e.g. non-small cell, small cell), lymphoma (e.g. AIDS-related, Burkitt, cutaneous T-cell Hodgkin, non-Hodgkin, primary central nervous system), medulloblastoma, melanoma, Merkel cell carcinoma, mesothelioma, metastatic squamous neck cancer, mouth cancer, multiple endocrine neoplasia syndrome, multiple myeloma, mycosis fungoides, myelodysplastic syndromes, myelodysplastic/myeloproliferative diseases, myelogenous leukemia, myeloid leukemia, myeloid leukemia, myeloproliferative disorders, chronic, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma, ovarian cancer, pancreatic cancer, pancreatic cancer, paranasal sinus and nasal cavity cancer, parathyroid cancer, penile cancer, pharyngeal cancer, pheochromocytoma, pineal astrocytoma and/or germinoma, pineoblastoma and supratentorial primitive neuroectodermal tumors, pituitary adenoma, plasma cell neoplasia/multiple myeloma, pleuropulmonary blastoma, primary central nervous system lymphoma, prostate cancer, rectal cancer, renal cell carcinoma (kidney cancer), renal pelvis and ureter, retinoblastoma, rhabdomyosarcoma, salivary gland cancer, sarcoma (e.g. Ewing family, Kaposi, soft tissue, uterine), Sezary syndrome, skin cancer (e.g. nonmelanoma, melanoma, merkel cell), small cell lung cancer, small intestine cancer, soft tissue sarcoma, squamous cell carcinoma, squamous neck cancer, stomach cancer, supratentorial primitive neuroectodermal tumor, t-cell lymphoma, testicular cancer, throat cancer, thymoma and thymic carcinoma, thyroid cancer, trophoblastic tumors, ureter and renal pelvis cancers, urethral cancer, uterine cancer, uterine sarcoma, vaginal cancer, visual pathway and hypothalamic glioma, vulvar cancer, Waldenström macroglobulinemia, and Wilms tumor.

In one embodiment, the cancer is AML. AML is the second most common leukemia, with approximately 13,000 newly diagnosed cases and 9,000 deaths annually in the US. Although approved therapies exist, the prognosis of many leukemia patients is poor and the likelihood of successful treatment is low. The current standard of care for AML is induction cytosine arabinoside (ara-C) in combination with an anthracycline agent (such as, for example, daunarubicin, idarubicine or mitoxantrone). This therapeutic regimen is typically followed by administration of high dose cytarabine and/or stem cell transplantation. These treatments have improved outcomes in young patients. Progress has also been made in the treatment of acute promyelocytic leukemia, where targeted therapy with all-trans retinoic acid (ATRA) or arsenic trioxide have resulted in excellent survival rates. However, patients over 60, a population which represents the vast majority of AML cases, remain a therapeutic enigma. Although 65-85% of patients initially respond to existing treatments, 65% of such responders undergo relapse, and many patients succumb to the disease. For at least this reason, and because the afore-mentioned treatments may have severe side effects, the inventive predictive test can guide use of the treatment that mitigates these litigations. In some embodiments, the present invention improves the likelihood of successful treatment by matching the right patient to the right treatment. Further, there are currently no tests to predict AML patient response to treatment.

The term subject, as used herein unless otherwise defined, is a mammal, e.g., a human, mouse, rat, hamster, guinea pig, dog, cat, horse, cow, goat, sheep, pig, or non-human primate, such as a monkey, chimpanzee, or baboon. The terms "subject" and "patient" are used interchangeably.

Exemplary Specimens

In certain embodiments, the specimen is a human tumor-derived cell line. In certain embodiments, the specimen is a cancer stem cell. In other embodiments, the specimen is derived from the biopsy of a solid tumor, such as, for example, a biopsy of a colorectal, breast, prostate, lung, pancreatic, renal, or ovarian primary tumor.

In certain embodiments, the specimen is derived from the biopsy of a non-solid tumor, such as, for example, any of the cancer described herein. In specific embodiments, the specimen is derived from the biopsy of a patient with multiple myeloma, acute myelogenous leukemia, acute lymphocytic leukemia, chronic lymphogenous leukemia, mantle cell lymphoma, diffuse large B-cell lymphoma, and non-Hodgkin's lymphoma. In a specific embodiment, the specimen is a multiple myeloma cell that is enriched by selection from a biopsy sample with an anti-CD138 antibody bound to a solid matrix or bead. In a specific embodiment, the specimen is an acute myelogenous leukemia cell that is enriched by binding to a CD45-directed antibody. In a specific embodiment, the specimen is a chronic lymphogenous leukemia or diffuse large B-cell lymphoma that is enriched by non-B cell depletion.

In some embodiments, the specimen is derived from a circulating tumor cell.

BH3 Profiling

In various embodiments, the invention comprises BH3 profiling. In various embodiments, the invention comprises BH3 profiling in which at least two, or three, or four, or five, or six, or seven, or eight, or nine, or ten BH3 peptides are evaluated at once. In some embodiments, the present methods comprise a multipeptide analysis, as opposed to an evaluation of a single BH3 peptide. In some embodiments, a panel of BH3 peptides is screened on a single patient specimen.

BH3 profiling and reagents useful for such a method is described in U.S. Pat. Nos. 7,868,133; 8,221,966; and 8,168,755 and US Patent Publication No. 2011/0130309, the contents of which are hereby incorporated by reference in their entireties.

Briefly, without wishing to be bound by theory, as a result of aberrant phenotypes, cancer cells develop functional blocks in apoptosis pathways. These blocks make cancer cells both resistant to some therapies, and, surprisingly, make some cancer cells sensitive to other therapies. The concept of "oncogene addiction" describes the phenomena of the acquired dependence of cancer cells on, or addiction to, particular proteins for survival. BH3 profiling determines if such a dependence on certain apoptosis regulating proteins occurs in given cancer cells, and identifies the dependent protein. Cancer cells can be, but are not always, pre-set to undergo apoptosis and this is a function of these cells being dependent on any, or all of the anti-apoptotic BCL-2 family proteins for their otherwise unintended survival. This provides insight into the likelihood of a cancer cell to respond to treatment.

Cancer cells, without wishing to be bound by theory, exhibit abnormalities, such as DNA damage, genetic instability, abnormal growth factor signaling, and abnormal or missing matrix interactions, any of which should typically induce apoptosis through the intrinsic (mitochondrial) apoptosis pathway. However, rather than respond to these apoptosis signals, cancer cells survive. Often, in doing so, these cells become highly dependent on selected blocks to chronic apoptosis signals. This adaptation provides a survival mechanism for the cancer cells; however, these adaptations can also make cancer cells susceptible to particular apoptosis inducing therapies. A crucial event that commits a cell to die by intrinsic apoptosis is the permeabilization of the mitochondrial outer membrane (MOMP) and the release of molecules that activate the effector caspases. In many cases, MOMP is the point of no return in the intrinsic apoptosis pathway. The BCL-2 family proteins are the key regulators of MOMP, and their activity is linked to the onset of lymphoid and several solid tumor cancers and is believed in many cancers to be the key mediator of resistance to chemotherapy.

BCL-2 proteins are regulated by distinct protein-protein interactions between pro-survival (anti-apoptotic) and pro-apoptotic members. These interactions occur primarily through BH3 (BCL-2 homology domain-3) mediated binding. Apoptosis-initiating signaling occurs for the most part upstream of the mitochondria and causes the translocation of short, BH3-only, BCL-2 family members to the mitochondria where they either activate or sensitize MOMP. The activator BH3 only proteins, BIM and Bid, bind to and directly activate the effector, pro-apoptotic proteins Bax and Bak, and also bind to and inhibit the anti-apoptotic BCL-2 family proteins, BCL-2, MCL1, Bfl-1, BCL-w and BCL-xL. The sensitizer BH3 proteins, Bad, Bik, NOXA, Hrk, Bmf, and Puma bind only to the anti-apoptotic BCL-2 family proteins, BCL-2, MCL1, Bfl-1, BCL-w, and BCL-xL, thereby blocking their anti-apoptotic functions. Without wishing to be bound by theory, each sensitizer protein has a unique specificity profile. For example, NOXA (A and B) bind with high affinity to MCL1, Bad binds to BCL-xL and BCL-2 but only weakly to MCL1, and Puma binds well to all three targets. An anti-apoptotic function of these proteins is the sequestering of the activator BH3 protein BIM and Bid. Displacement of these activators by sensitizer peptides results in Bax/Bak-mediated apoptotic commitment. These interactions can have various outcomes, including, without limitation, homeostasis, cell death, sensitization to apoptosis, and blockade of apoptosis.

A defining feature of cancer cells in which apoptotic signaling is blocked is an accumulation of the BH3 only activator proteins at the mitochondrial surface, a result of these proteins being sequestered by the anti-apoptotic proteins. This accumulation and proximity to their effector target proteins accounts for increased sensitivity to antagonism of BCL-2 family proteins in the "BH3 primed" state.

In some embodiments, a cell yielding a high apoptotic response to NOXA (A or B) is MCL1 primed, while a high response to the peptide Bad indicates that BCL-xL or BCL-2 provides the apoptotic block. In some embodiments, Puma reflects pan-BCL-2 family priming. In this way, cells that are dependent on either MCL1 or BCL-xL, on both proteins, or on several BCL-2 family members are readily distinguished so that appropriate treatment may be tailored accordingly. The distinctions in mitochondrial response to these peptides guide the use of therapies that are known to work through pathways that funnel into either MCL1 or BCL-xL affected intrinsic signaling. The use of a BCL-2 inhibiting or a MCL1 inhibiting compound may be indicated in such cases. In some embodiments, the present methods also indicate or contraindicate therapies that target entities upstream of MCL1 or BCL-xL.

BH3 profiling assay identifies when a cancer cell is in the primed state, as well as in which configuration the priming has occurred, and this has predictive value.

Exemplary Clinical Factors and Additional Biomarkers

In some embodiments, the invention comprises the evaluation of clinical factors. In some embodiments, the invention comprises an evaluation of BH3 profiling and/or clinical factors to assess a patient response. In some embodiments, a clinical factor that provides patient response information in combination with a BH3 profiling study may not be linked to apoptosis. In some embodiments, a clinical factor is non-apoptosis affecting. In one embodiment, the clinical factor is one or more of age, cytogenetic status, performance, histological subclass, gender, and disease stage. In one embodiment, the clinical factor is shown in Table 3.

In one embodiment, the clinical factor is age. In one embodiment, the patient age profile is classified as over about 10, or over about 20, or over about 30, or over about 40, or over about 50, or over about 60, or over about 70, or over about 80 years old.

In one embodiment, the clinical factor is cytogenetic status. In some cancers, such as Wilms tumor and retinoblastoma, for example, gene deletions or inactivations are responsible for initiating cancer progression, as chromosomal regions associated with tumor suppressors are commonly deleted or mutated. For example, deletions, inversions, and translocations are commonly detected in chromosome region 9p21 in gliomas, non-small-cell lung cancers, leukemias, and melanomas. Without wishing to be bound by theory, these chromosomal changes may inactivate the tumor suppressor cyclin-dependent kinase inhibitor 2A. Along with these deletions of specific genes, large portions of chromosomes can also be lost. For instance, chromosomes 1p and 16q are commonly lost in solid tumor cells. Gene duplications and increases in gene copy numbers can also contribute to cancer and can be detected with transcriptional analysis or copy number variation arrays. For example, the chromosomal region 12q13-q14 is amplified in many sarcomas. This chromosomal region encodes a binding protein called MDM2, which is known to bind to a tumor suppressor called p53. When MDM2 is amplified, it prevents p53 from regulating cell growth, which can result in tumor formation. Further, certain breast cancers are associated with overexpression and increases in copy number of the ERBB2 gene, which codes for human epidermal growth factor receptor 2. Also, gains in chromosomal number, such as chromosomes 1q and 3q, are also associated with increased cancer risk.

Cytogenetic status can be measured in a variety of manners known in the art. For example, FISH, traditional karyotyping, and virtual karyotyping (e.g. comparative genomic hybridization arrays, CGH and single nucleotide polymorphism arrays) may be used. For example, FISH may be used to assess chromosome rearrangement at specific loci and these phenomena are associated with disease risk status. In some embodiments, the cytogenetic status is favorable, intermediate, or unfavorable as determined by classification systems including, but not limited to the Southwest Oncology Group (SWOG), the Medical Research Council (MRC), and the Cancer and Leukemia Group B (CALGB).

In one embodiment, the clinical factor is performance. Performance status can be quantified using any system and methods for scoring a patient's performance status are known in the art. The measure is often used to determine whether a patient can receive chemotherapy, adjustment of dose adjustment, and to determine intensity of palliative care. There are various scoring systems, including the Karnofsky score and the Zubrod score. Parallel scoring systems include the Global Assessment of Functioning (GAF) score, which has been incorporated as the fifth axis of the Diagnostic and Statistical Manual (DSM) of psychiatry. Higher performance status (e.g., at least 80%, or at least 70% using the Karnofsky scoring system) may indicate treatment to prevent progression of the disease state, and enhance the patient's ability to accept chemotherapy and/or radiation treatment. For example, in these embodiments, the patient is ambulatory and capable of self-care. In other embodiments, the evaluation is indicative of a patient with a low performance status (e.g., less than 50%, less than 30%, or less than 20% using the Karnofsky scoring system), so as to allow conventional radiotherapy and/or chemotherapy to be tolerated. In these embodiments, the patient is largely confined to bed or chair and is disabled even for self-care.

The Karnofsky score runs from 100 to 0, where 100 is "perfect" health and 0 is death. The score may be employed at intervals of 10, where: 100% is normal, no complaints, no signs of disease; 90% is capable of normal activity, few symptoms or signs of disease, 80% is normal activity with some difficulty, some symptoms or signs; 70% is caring for self, not capable of normal activity or work; 60% is requiring some help, can take care of most personal requirements; 50% requires help often, requires frequent medical care; 40% is disabled, requires special care and help; 30% is severely disabled, hospital admission indicated but no risk of death; 20% is very ill, urgently requiring admission, requires supportive measures or treatment; and 10% is moribund, rapidly progressive fatal disease processes.

The Zubrod scoring system for performance status includes: 0, fully active, able to carry on all pre-disease performance without restriction; 1, restricted in physically strenuous activity but ambulatory and able to carry out work of a light or sedentary nature, e.g., light house work, office work; 2, ambulatory and capable of all self-care but unable to carry out any work activities, up and about more than 50% of waking hours; 3, capable of only limited self-care, confined to bed or chair more than 50% of waking hours; 4, completely disabled, cannot carry on any self-care, totally confined to bed or chair; 5, dead.

In one embodiment, the clinical factor is histological subclass. In some embodiments, histological samples of tumors are graded according to Elston & Ellis, Histopathology, 1991, 19:403-10, the contents of which are hereby incorporated by reference in their entirety.

In one embodiment, the clinical factor is gender. In one embodiment, the gender is male. In another embodiment, the gender is female.

In one embodiment, the clinical factor is disease stage. By way of non-limiting example, using the overall stage grouping, Stage I cancers are localized to one part of the body; Stage II cancers are locally advanced, as are Stage III cancers. Whether a cancer is designated as Stage II or Stage III can depend on the specific type of cancer. In one non-limiting example, Hodgkin's disease, Stage II indicates affected lymph nodes on only one side of the diaphragm, whereas Stage III indicates affected lymph nodes above and below the diaphragm. The specific criteria for Stages II and III therefore differ according to diagnosis. Stage IV cancers have often metastasized, or spread to other organs or throughout the body.

In some embodiments, the clinical factor is the French-American-British (FAB) classification system for hematologic diseases (e.g. indicating the presence of dysmyelopoiesis and the quantification of myeloblasts and erythroblasts). In one embodiment, the FAB for acute lymphoblastic leukemias is L1-L3, or for acute myeloid leukemias is M0-M7.

In another embodiment, the method further comprises a measurement of an additional biomarker selected from mutational status, single nucleotide polymorphisms, steady state protein levels, and dynamic protein levels. In another embodiment, the method further comprises predicting a clinical response in the patient. In another embodiment, the clinical response is about 1, about 2, about 3, or about 5 year progression/event-free survival.

A variety of clinical factors have been identified, such as age profile and performance status. A number of static measurements of diagnosis have also been utilized, such as cytogenetics and molecular events including, without limitation, mutations in the genes MLL, AML/ETO, Flt3-ITD, NPM1 (NPMc+), CEBPα, IDH1, IDH2, RUNX1, RAS, and WT1 and in the epigenetic modifying genes TET2 and ASXL, as well as changes in the cell signaling protein profile.

In some embodiments, the preventive methods comprise administering a treatment to a patient that is likely to be afflicted by cancer as guided by the methods described herein. In some embodiments, a subject is likely to be afflicted by cancer if the subject is characterized by one or more of a high risk for a cancer, a genetic predisposition to a cancer (e.g. genetic risk factors), a previous episode of a cancer (e.g. new cancers and/or recurrence), a family history of a cancer, exposure to a cancer-inducing agent (e.g. an environmental agent), and pharmacogenomic information (the effect of genotype on the pharmacokinetic, pharmacodynamic or efficacy profile of a therapeutic).

In some embodiments, a subject is likely to be afflicted by cancer if the subject is characterized by a high risk for a cancer. In some embodiments, a subject is likely to be afflicted by cancer if the subject is characterized by a genetic predisposition to a cancer. In some embodiments, a genetic predisposition to a cancer is a genetic clinical factor, as is known in the art. Such clinical factors may include, by way of example, HNPCC, MLH1, MSH2, MSH6, PMS1, PMS2 for at least colon, uterine, small bowel, stomach, urinary tract cancers. In some embodiments, a subject is likely to be afflicted by cancer if the subject is characterized by a previous episode of a cancer. In some embodiments, the subject has been afflicted with 1, or 2, or 3, or 4, or 5, or 6, previous episodes of cancer. In some embodiments, a subject is likely to be afflicted by cancer if the subject is characterized by a family history of a cancer. In some embodiments, a parent and/or grandparent and/or sibling and/or aunt/uncle and/or great aunt/great uncle, and/or cousin has been or is afflicted with a cancer. In some embodiments, a subject is likely to be afflicted by cancer if the subject is characterized by exposure to a cancer-inducing agent (e.g. an environmental agent). For example, exposing skin to strong sunlight is a clinical factor for skin cancer. By way of example, smoking is a clinical factor for cancers of the lung, mouth, larynx, bladder, kidney, and several other organs.

Further, in some embodiments, any one of the following clinical factors may be useful in the methods described herein: gender; genetic risk factors; family history; personal history; race and ethnicity; features of the certain tissues; various benign conditions (e.g. non-proliferative lesions); previous chest radiation; carcinogen exposure and the like.

Further still, in some embodiments, the any one of the following clinical factors may be useful in the methods described herein: one or more of a cell surface marker CD33, a cell surface marker CD34, a FLT3 mutation status, a p53 mutation status, a phosphorylation state of MEK-1 kinase, and phosphorylation of serine at position 70 of BCL-2.

In some embodiments, the clinical factor is expression levels of the cytokines, including, without limitation, interleukin-6. In some embodiments, interleukin-6 levels will correlate with likelihood of response in MM patients, including a poor patient prognosis or a good patient prognosis.

In certain embodiments, the likelihood of response is determined by assessing percent priming. In certain embodiments, the priming is defined by the following equation:

$$\% \text{ Priming} = \left[100 * \left(\frac{DMSO\ AUC - Peptide_1 AUC}{DMSO\ AUC - CCCP_{avg} AUC}\right)\right] Peptide_1 + \left[100 * \left(\frac{DMSO\ AUC - Peptide_2 AUC}{DMSO\ AUC - CCCP_{avg} AUC}\right)\right] Peptide_2 + \ldots / (n \text{ peptides})$$

in which the AUC comprises either area under the curve or signal intensity; the DMSO comprises the baseline negative control; and the CCCP (Carbonyl cyanide m-chlorophenyl hydrazone) comprises an effector of protein synthesis by serving as uncoupling agent of the proton gradient established during the normal activity of electron carriers in the electron transport chain in the mitochondria comprises the baseline positive control. In some embodiments, the area under the curve is established by homogenous time-resolved fluorescence (HTRF). In some embodiments, the time occurs over a window from between about 0 to about 300 min to about 0 to about 30 min. In some embodiments, the area under the curve is established by fluorescence activated cell sorting (FACS) by measuring the median fluorescence intensity (MFI) statistic. In some embodiments, the signal intensity is a single time point measurement that occurs between about 5 min and about 300 min.

In another embodiment, the method comprises measuring the BH3 profiling assay and one or more of a cell surface marker CD33, a cell surface marker CD34, a FLT3 mutation status, a p53 mutation status, a phosphorylation state of MEK-1 kinase, and phosphorylation of serine at position 70 of BCL-2; and correlating to efficacy in treating AML patients with cytarabine or cytarabine-based chemotherapy and/or azacitidine.

In another embodiment, the method comprises measuring the BH3 profiling assay and one or more of a cell surface marker CD33, a cell surface marker CD34, a FLT3 mutation status, a p53 mutation status, a phosphorylation state of MEK-1 kinase, and phosphorylation of serine at position 70 of BCL-2; and correlating to efficacy in treating MM patients with chemotherapy.

In still another embodiment, the cancer is AML and/or MM and the clinical factor is age profile and/or cytogenetic status; or the cancer is AML and/or MM and the cancer treatment is cytarabine or cytarabine-based chemotherapy and/or azacitidine, or the cancer treatment is cytarabine or cytarabine-based chemotherapy and/or azacitidine and the clinical factor is age profile and/or cytogenetic status, or the cancer treatment is cytarabine or cytarabine-based chemotherapy and/or azacitidine; the cancer is AML and/or MM; and the clinical factor is age profile and/or cytogenetic status.

The invention also provides kits that can simplify the evaluation of tumor or cancer cell specimens. A typical kit of the invention comprises various reagents including, for example, one or more agents to detect a BH3 peptide. A kit may also comprise one or more of reagents for detection, including those useful in various detection methods, such as, for example, antibodies. The kit can further comprise materials necessary for the evaluation, including welled plates, syringes, and the like. The kit can further comprise a label or printed instructions instructing the use of described reagents. The kit can further comprise a treatment to be tested.

The term "about" when used in connection with a referenced numeric indication means the referenced numeric indication plus or minus up to 10% of that referenced numeric indication. For example, the language "about 50" covers the range of 45 to 55.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features. Although the open-ended term "comprising," as a synonym of terms such as including, containing, or having, is used herein to describe and claim the invention, the present technology, or embodiments thereof, may alternatively be described using more limiting terms such as "consisting of" or "consisting essentially of" the recited ingredients.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

This invention is further illustrated by the following non-limiting examples.

Examples

Example 1: Studies Using AML Patient-Based Cohorts

We obtained a total of 63 peripheral blood and bone marrow samples from newly diagnosed patients with AML or MDS enrolled on protocols NCT00795002 (J0856), NCT00407966 (J0669), or NCT01349972 (J1101). Patients were treated with FLAM: alvocidib (Flavopiridol), Ara-C and Mitoxantrone (n=54) or 7+3 (Ara C and Daunorubicin, n=9). Complete response, characterized by less than 5% myeloblasts with normal maturation of all cell lines, an ANC ≥1000/µL and platelet count ≥100,000/µL, absence of blast in peripheral blood, absence of leukemic cells in the marrow, clearance of cytogenetics associated with disease, and clearance of previous extramedullary disease. Overall patient characteristics were provided by blind external review after BH3 profiling was completed and are summarized in Table 1, including patient age, cytogenetic risk, FLT-3 mutation, NPM1 Mutation, MDS/Marrow Disorder History, Prior Chemotherapy History, BM Blast %, WBC Count at Diagnosis, and response to the therapy. Individual patient characteristics are listed in Table 2.

Mitochondrial Profiling

Briefly, frozen, extracted leukocyte samples were rapidly thawed, and cell viability was determined by Trypan Blue exclusion. Cells were washed in FACS buffer (1x PBS with 2% FBS) and immunophenotyped using fluorescently labeled CD45, CD3, and CD20 monoclonal antibodies. Cells were then resuspended in Newmeyer buffer (10 mM Trehalose, 10 mM HEPES, 80 mM KCl, 20 µM EGTA, 20 µM EDTA, 5 mM succinate, pH 7.4) for the perturbation step. The BH3 peptides were diluted in Newmeyer buffer to make working solutions resulting in final concentrations of: BIM (100 µM), BIM (0.1 µM), NOXA (100 µM), Puma (10 µM), HRK (100 µM), BAD (100 µM), and BID (1.0 µM). DMSO and CCCP were used as negative and positive peptide controls. Digitonin and oligomycin were added to individual FACS tubes, followed by the BH3 peptides. Cells were then added to the FACS tubes and incubated for 2 hours and 15 minutes at room temperature, in order for cell permeabilization, delivery of peptides or compounds, and mitochondrial depolarization to occur. After the incubation, JC-1 dye was prepared in Newmeyer buffer and added to directly to the treated cells. An additional tube of cells that was not treated with a peptide or compound was stained with propidium iodide (PI) to ensure that cells were effectively permeabilized by the digitonin. After 45 minutes of incubation with JC-1, cells were analyzed on a three laser BD FACSCanto II. AML Blasts were gated based on four parameters: 1) permeabilization (as determined by PI staining), 2) singlet discrimination based on SSC, 3) CD45 dim and CD3/CD20 negative, and 4) SSC low. The median JC-1 red fluorescence of the gated blast population was then used to calculate % depolarization as compared to DMSO (negative) and CCCP (positive) controls.

Cytogenetic Risk Status Determination

Individual Patient cytogenetic risk classification (Favorable, Intermediate, and Adverse) was determined from the Cancer and Leukemia Group B (CALGB) guidelines: Favorable=inv16, t(8:21), t(15;17) intermediate=diploid, Unfavorable=−5, −7, +8, t(6;9), 11q, PH1+, ≥3 unrelated cytogenetic abnormalities, etc.

Statistical Analysis:

For each peptide, the percentage priming was calculated using the following formula that determines the priming based on the DMSO negative control as completely unprimed and the CCCP as a 100% primed reference:

$$\text{Percentage Priming} = \left[1 - \frac{(\text{Peptide} - CCCP)}{(DMSO - CCCP)}\right] \times 100$$

For analysis, all patients not classified as CR were treated as non-responders [Minimal Residual Disease (MRD), Partial Remission (PR), and TF (treatment failure)]. Student's t-tests, Mann-Whitney rank-sum non-parametric tests, multi-variate logistic regression, and ROC curve analyses, between the BH3 peptides (and other tumor characteristics, such as cytogenetics, etc.) and response, were calculated using GraphPad Prism Version 5.04 and MedCalc Version 14.8.1.

Mitochondrial Profiling of AML Patient Samples Enrolled on FLAM Protocols

A total of 63 patient samples were received and processed, and those samples are summarized in Tables 1 and 2. Full profiles were obtained from 43 of the samples, and an additional nine (9) were processed with subsets of the profiles (due to insufficient cell numbers to perform the entire assay). The remaining eleven (11) samples were of insufficient quality to determine any BH3 profiling, either due to poor signal to noise ratios (cells were already apoptotic before the assay) or inadequate cell numbers. All subsequent analyses were performed only on those samples that were successfully processed for any BH3 profiling (n=52 total).

The clinical variables obtained from the patients were compared to response to determine which, if any, of these factors influenced whether patients would respond to the therapies or not (Table 3). The only variable that was found to have a significant association with CR was the cytogenetic risk factor, where those with adverse classifications being less likely to respond to the therapies. The WBC, history of MDS, and which protocol was followed were all close to being significant, with higher WBC values and a history of MDS being associated with response to therapy. Protocol J0856 had a higher CR rate (13 CRs in 25 patients) than J1101 (8 of 25), and protocol J0669 was only represented by two patients that were successfully BH3 profiled. Age, BM Blast percentage, and NPM/FLT-3 mutation status were not significantly associated with response in this dataset.

All BH3 individual patient data is summarized in Table 4 and details each BH3 peptide's ability to induce mitochondrial depolarization in the blast cells (i.e., "prime"). Looking at all of the responses, the BIM 100 µM peptide resulted in the highest median depolarization (99.2% priming) and NOXA had the lowest overall depolarization (16.0% priming). The single peptide BH3 profiles were then compared in the patients who responded to treatment (CR) to those who did not (NR) in Table 6. No single peptide was significantly associated with response; however, the BAD peptide approached significance with a p-value of 0.09, but only had an AUC value of 0.65. This indicates that using the entire patient set, no individual BH3 peptide is sufficient to identify patients who respond to the FLAM treatment.

The BH3 peptides were tested in multivariate analysis with other BH3 peptide profiles and with the clinical variables (Table 8). This analysis reveals that a strongly significant association between BIM 100 µM plus BAD plus PUMA exists in relation to response, with a p-value of 0.009 and a ROC AUC of 0.732 (FIG. 1). When these three peptides are combined with cytogenetic risk category, the p-value becomes 0.0001 with an AUC of 0.84. Further addition of the MDS history to the analysis creates further significance with a p-value of 0.0001 and an AUC of 0.85. Cytogenetic risk category alone only yields an AUC value of 0.60 (Cytogenetic risk plus MDS history gives an AUC of 0.72). This indicates that addition of the BH3 peptide priming to the analysis greatly increases the ability to identify those patients who respond to FLAM. At an ideal cutoff (Youden index—highest specificity plus sensitivity) using the BH3 peptide data along with cytogenetic risk category and MDS history, this assay is 89.5% sensitive and 76% specific at identifying patients who responded to treatment in this study. This indicates that using the BH3 peptide priming data from these three peptides along with clinical information could be valuable in predictive value for treatment with the FLAM regimen.

During the course of this study, we also examined other factors that may play a role in BH3 priming. Since the source of leukemic cells (i.e. peripheral blood or bone marrow) could potentially isolate different populations of cells, we performed analysis in only those samples that were obtained from the bone marrow of the patients. Table 8 shows the association of each BH3 peptide with response in only bone marrow samples. In this sample subset, NOXA priming is significantly (p=0.006) higher in patients that respond to treatment compared with those that did not (44.5% and 5.2% respectively) and has an AUC value of 0.805 (FIG. 2 and FIG. 3). None of the other single peptides showed significant association with response in the bone marrow samples alone. With a cutoff value of higher than 10.78% NOXA priming, the test is 92% sensitive and 67% specific. Addition of cytogenetic risk factor and MDS history to the algorithm shows that NOXA priming adds to these variables in predicting response to treatment, and yields an AUC value of 0.92 with a sensitivity of 92% and specificity of 80% at an ideal cutoff value (Table 8 and FIG. 3).

The results of this study establish that BH3 profiling is useful for identifying patients that are likely to respond to the FLAM treatment. Looking at the entire dataset, while individual BH3 peptides did not correlate with response, combinations of several peptides (BIM, BAD, and PUMA) did show strong correlations with FLAM response. These several peptides showed correlations with response in both the bone marrow and peripheral blood samples within the study. Moreover, these data were additive to known patient risk factors, allowing us to identify an algorithm incorporating the cytogenetic status along with the MDS history of the patient into a single metric that predicts the patient response.

Another interesting finding of this study is that while NOXA signaling was not found to be significantly associated with FLAM response in the entire dataset. However, examination of the bone marrow samples alone showed very strong associations with response. As the niche of AML tumor cells would be the bone marrow, it is not surprising that there would be different BH3 profiles in the peripheral blood compared with the bone marrow, as phenotypic markers of blasts can be different in the peripheral blood compared with the bone marrow (1,2). Additionally, bone marrow stroma has previously been shown to confer resistance to AML cells to various therapies through direct cell contact and through soluble factors present in the bone marrow (3). Since the bone marrow draw would potentially collect AML blasts, soluble factors, and potentially the actual stromal cells, the BH3 priming assay in bone marrow may represent a more direct test of the leukemic cells in their normal environmental context. Functional differences have previously been observed in AML with FLT3 kinase inhibitor monotherapy, where circulating blasts are cleared from the peripheral blood by the therapy while bone marrow blasts are minimally affected (4). The NOXA readout may be detecting a similar functional difference, where priming with NOXA results in MCL-1 displacement and leads to apoptosis to identify those cancers that are likely to respond to FLAM.

Both of the algorithms identified in this study, NOXA and [BAD+BIM 100+PUMA] priming, may be identifying cancer cells that are MCL-1 primed. A cell yielding a high apoptotic response to NOXA is said to be MCL-1 primed, while a high response to the peptide Bad indicates that BCL-xL or BCL-2 provides the apoptotic block. Since PUMA may reflect pan-BCL-2 family priming, and the algorithm behind [BAD+BIM 100+PUMA] is actually PUMA—BAD—BIM100, so in effect; both of these readings may be effectively measuring the priming state of MCL-1, and ultimately those patients that respond to the FLAM regimen may be MCL-1 dependent. One algorithm for determining likelihood of response to FLAM from this study is to identify patients above a certain threshold as likely responders, and then use this threshold to characterize the sensitivity, specificity, positive predictive value, and negative predictive value for the test. Inclusion of clinical adjustment variables to account for the patient or sample specific context can be done through the use of logistic regression models fitted to training data sets and then validated. Then, using that model, probabilities can be calculated using the sigmoid function with the logistic model; these probabilities can be used to identify thresholds to establish the test characteristics at those cutoff values in terms of specificity, sensitivity, positive predictive value, and negative predictive value. Decision trees may also be used, which would take into account any of the patient or sample characteristics and BH3 profiling results to establish likelihood of response. Other algorithms may also be used to develop predictive algorithms including patient and sample characteristics, including but not limited to, random forests, neural networks, and boosting.

Example 2: Algorithm to Discern Between a FLAM Regimen Versus a Traditional 7+3 Treatment Strategy BIM 0.1 priming in AML patient bone marrow or peripheral blood was correlated with response to the 7+3 regimen (cytarabine plus anthracycline); See Pierceall, et al. "BH3 Profiling Discriminates Response to Cytarabine-based Treatment of Acute Myelogenous Leukemia" Molecular Cancer Therapeutics. As discussed above, NOXA bone marrow priming is correlated with response to the FLAM (alvocidib, ara-C, mitoxantrone) regimen. We investigated what algorithm would distinguish between whether FLAM or 7+3 should be used to treat naïve AML patients.

Figure 5A:
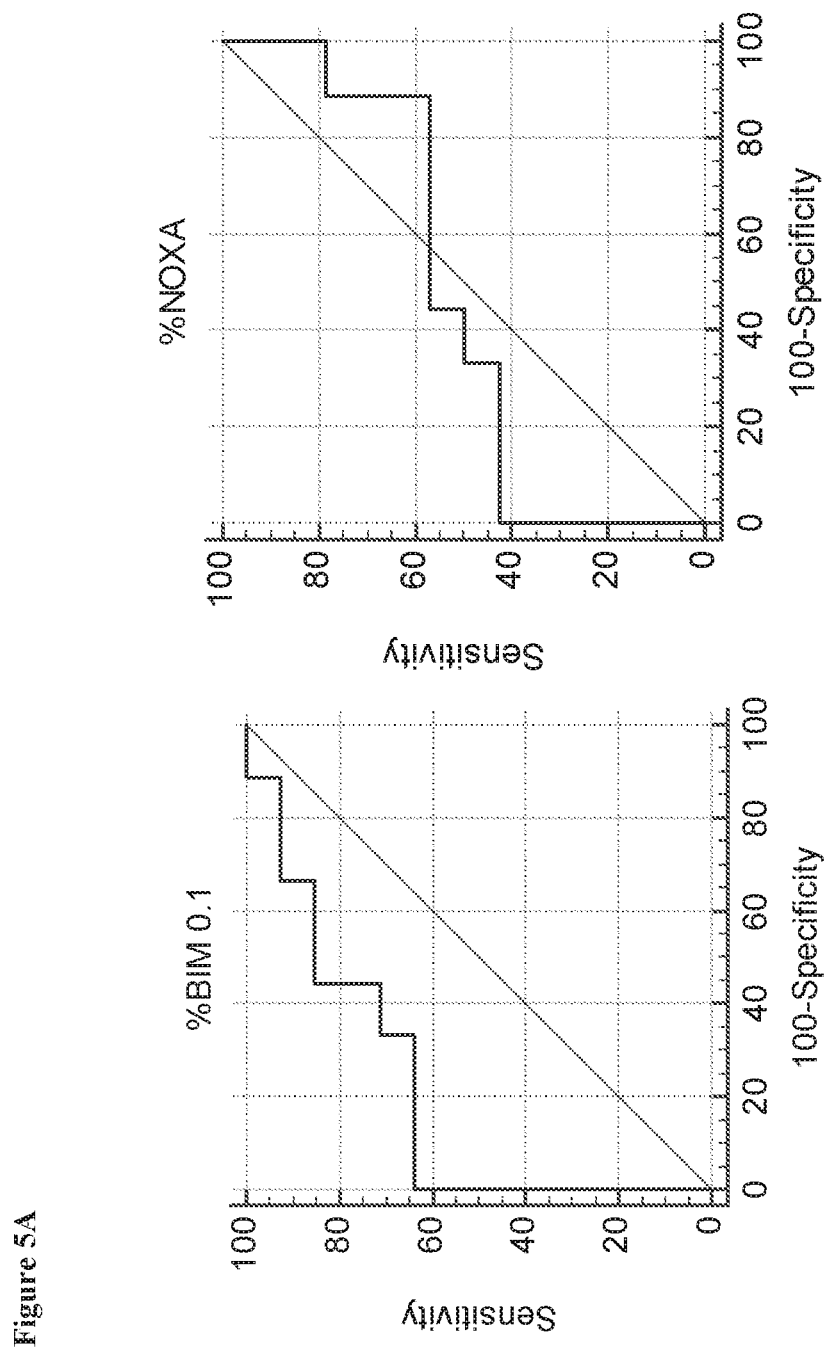

BIM 0.1 is predictive of response to 7+3 in a BM sample subset with an AUC value of 0.80 and sensitivity and specificity of 64.3% and 100% respectively—below left. However, in those same samples NOXA has essentially no predictive power with an AUC value of 0.54 and sensitivity and specificity of 42.9% and 100% specificity. See FIG. 5. (compared with an AUC of 0.81 and 92%/67% sensitivity/specificity when treated with FLAM). This indicates that NOXA priming, when detected in bone marrow cells taken from pretreatment AML patients, is correlated with response to FLAM and not 7+3, and that the BIM 0.1 reading from the peripheral blood of AML patients tested prior to treatment is correlated with response to 7+3 and not FLAM.

Figure 6:
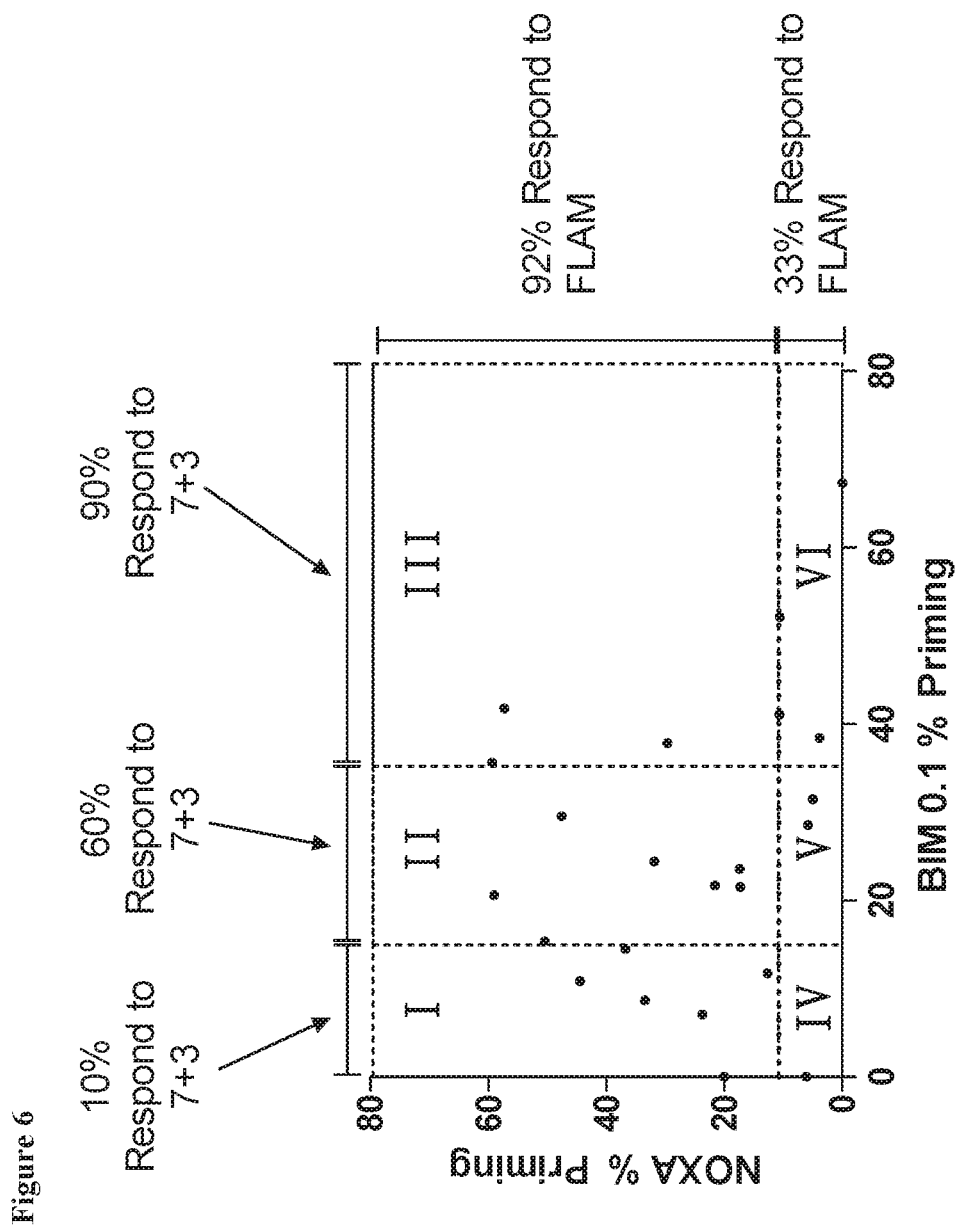
FIG. 6 shows a method for identifying an algorithm for selecting between cancer therapies in a treatment-naïve AML patient. By comparing the relative BIM 0.1 and NOXA profiling, the patient can be assigned to FLAM therapy, 7+3 therapy, or is identified as not suitable for either therapy.

Further examination of the NOXA priming compared with the BIM 0.1 priming reveals that there are subclasses of patients with priming values that indicate they are unlikely to respond one agent but likely to respond to another. FIG. 6 illustrates the NOXA priming versus the BIM 0.1 priming from bone marrow samples from the original 7+3 study (n=23). The data in FIG. 6 provide a method of selecting between cancer therapy strategies in a pre-treatment AML patient by comparing NOXA priming in a bone marrow sample versus BIM 0.1 priming in a peripheral blood (PB) sample of the patient. If the BM NOXA >10.8% and BM/PB BIM 0.1<35% then the patient is a candidate for FLAM. If the BM NOXA is <10.8% and BM/PB BIM 0.1 >15% then patient is a candidate for 7+3 therapy. The patient is also a candidate for 7+3 therapy where BM NOXA <10.8% and BM/PB BIM 0.1 >35%. Finally, where BM NOXA <10.8% and BM/PB BIM 0.1<15% the patient is not a candidate for either FLAM or 7+3 therapy.

We also confirmed that NOXA priming alone predicts AML patient survival in response to FLAM treatment. FIG. 10B. Using 40% NOXA priming as a cut-off in samples, patients having 40% or above NOXA priming have a much higher likelihood of having a complete response and surviving. This data confirms that AML patient response to FLAM treatment can be predicted using NOXA priming.

Figure 7:
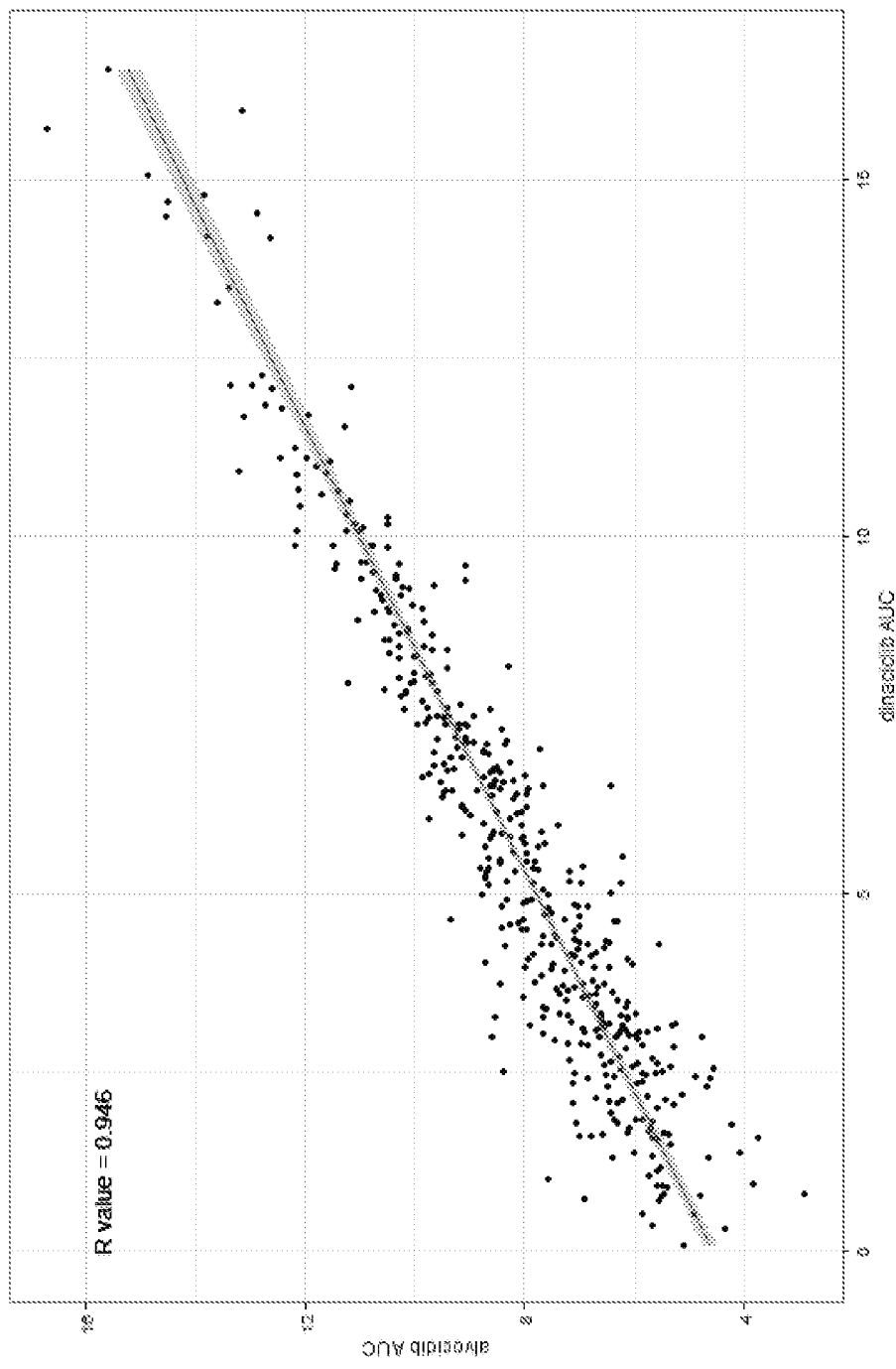
FIG. 7 Cell line response to pharmacologic agents was downloaded from the CTRP v2.0 drug screen. A total of 437 cell lines were tested with dinaciclib (inhibitor of CDK1, 2, 5, and 9) and with alvocidib (CDK9 inhibitor). Area under the curve values were calculated using 8 concentration points by numeric integration. Correlation between response to these agents was calculated using the Pearson method and was found to be about 0.95. These data illustrate that, due to the similarity between the two agents, NOXA biomarker are useful in predicting response to dinaciclib as well as alvocidib.

Example 3: NOXA Identifying PraediCare Dx™ Readouts Utility within Targeted Drug Class We have shown that particular mitochondrial readouts are associated with cellular response to particular treatments. In order to further assess the influence of cell context on variations in utility of mitochondrial readout we compared the activity of MCL-1 perturbing drugs on cancer cells grown in culture and compared to our understanding of the mitochondrial profiling readouts in cells collected from patients. We looked at the overlap in the range of cancer cell response of two therapeutic compounds that are within a target class correlate to the same readout in mitochondrial profiling. In one instance we looked at two CDK inhibiting compounds with prevalent activity against CDK9, alvocidib and dinaciclib. FIG. 7 illustrates that the NOXA readout is shown to predict response to each of these compounds, in the case of dinaciclib across cancer cell lines as referenced in FIG. 7). Response to alvocidib and dinaciclib in those cell lines was obtained from the cancer response therapeutics portal (www.broadinstitute.org/ctrp/) and cells were classified as responding to these compounds based on the AUC (Area under the curve) values obtained. As seen in FIG. 7, the overlap in the cell line response profile is striking, with a correlation coefficient of 0.95.

These data establish the utility of the NOXA priming test for multiple CDK inhibiting compounds with prevalent activity against CDK9.

Example 4: Ex Vivo Context NOXA Compounds

Figure 8:
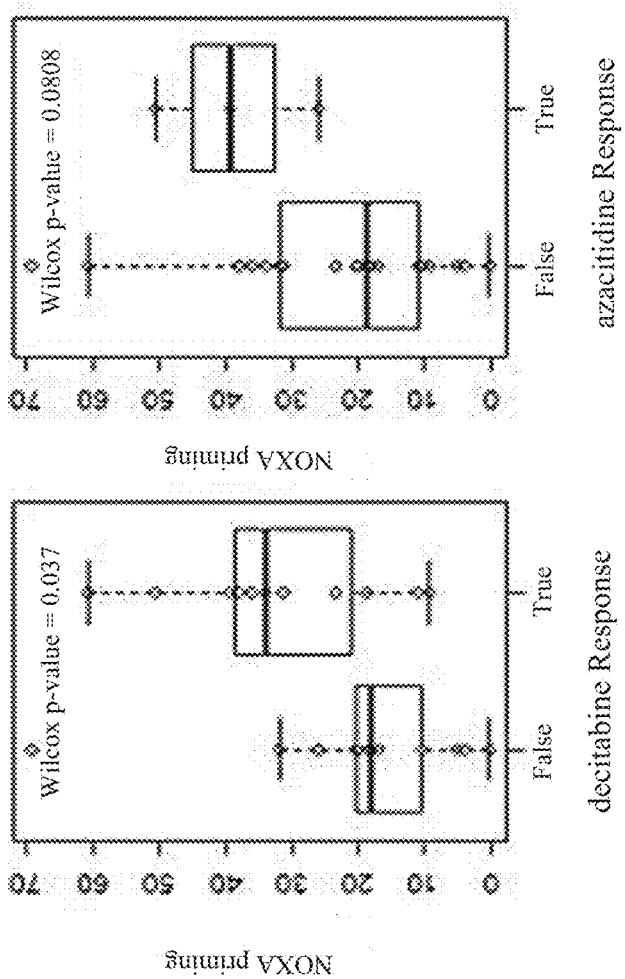
FIG. 8 shows the NOXA readout from AML samples representing the patient population 60 years old or older. The spread of the NOXA signal indicates a broad representation of signal across this representative population. The data shows that Higher MCL-1 Dependencies in cells determined by NOXA priming indicates greater sensitivity to hypomethylating agents (HMA). Cancer cell lines (n=33) were profiled for MCL-1 dependency with the NOXA peptide using the PraediCare Dx™ assay. Response to azacitidine and decitabine in those cell lines was obtained from the cancer response therapeutics portal (Broad Institute CTD2 public data base) and cells were classified as responding to the hypomethylating agents (HMAs) based on the AUC (Area under the curve) values obtained using the 40% quantile for decitabine and 12% quantiles for azacitidine as thresholds for response. Rank-sum test p-values were calculated between the two groups and are displayed on the plots. Together, this indicates that MCL-1 dependency through the NOXA biomarker may be required for response to HMAs.

Using publicly available therapeutic drug response data from cancer cell lines, additional therapeutic drug classes for which the NOXA biomarker may be important can be identified. To examine this possibility, we examined the utility in the NOXA priming readout for assessing cancer cell response to hypomethylating agents (HMAs) as an example. We found that the MCL-1 dependencies in cells determined by NOXA priming indicated greater sensitivity to these HMAs. Cancer cell lines (n=33) were profiled for MCL-1 dependency with the NOXA peptide using a FACS BH3 Profiling Assay (PraediCare Dx™ assay). Response to azacitidine and decitabine in those cell lines was obtained from the cancer response therapeutics portal (www.broadinstitute.org/ctrp/), and cells were classified as responding to the HMAs based on the response to the agents by AUC (Area under the curve) values obtained using the 40% quantile for decitabine and 12% quantiles for azacitidine as thresholds for response. Rank-sum test p-values were calculated between the two groups and are displayed on the plots. Together, this indicates that MCL-1 dependency through the NOXA biomarker may be required for response to HMAs (FIG. 8).

Example 5: Mutational Status Affects the Priming State and the Response Rate in AML Patients to Hypomethylating Agents and Other Drugs Though there are mutations in target proteins that completely align with drug activity and can guide treatment of targeted therapies, questions about relapse and toxicity, as well as best combination options require additional measurements, remain unanswered. During development, targeted agents are selected for on-target activity. There are usually also unexpected activities that cannot be directly explained by a mutational profile or gene expression pattern.

Within the leukemia field, a variety of prognostic genetic biomarkers have been identified including: FLT3, IDH, and p53 mutations for acute myeloid leukemia (AML) and IGHV, BCL-6, BTK, and p53 mutations for chronic lymphocytic leukemia (CLL). These biomarkers are generally associated with either a poor or favorable outcome to therapy in general. With the exception of small segments of the CLL population, the predictive value of these tests requires additional sensitivity so are not used to guide therapy selection. The mechanism of many common drugs and the patient's response to those agents frequently depends on the ability of the cancer cells to respond to pro-apoptotic signaling. Even in the context of a mutation that is associated with drug response, there is variability between patients in respect to response, so measuring the degree of apoptotic pre-disposition in cancer is key.

Figure 11B:
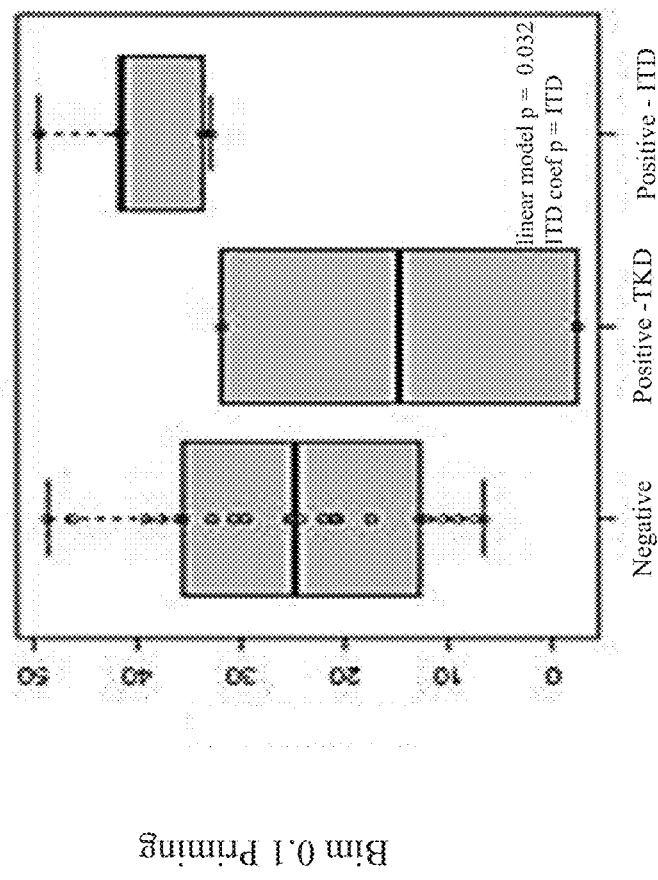
Figure 12A:
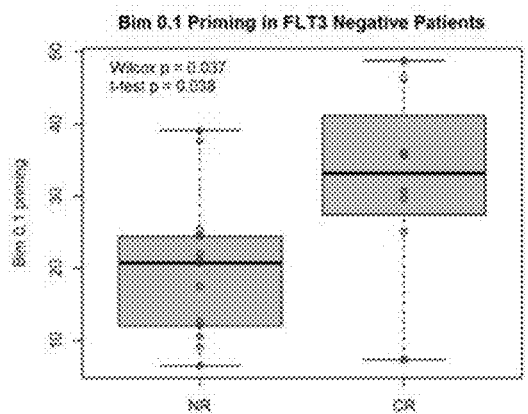
FIGS. 12A-12D shows aspects of the relationship between FLT3 Mutational Status, priming and response to decitabine.
Figure 12B:
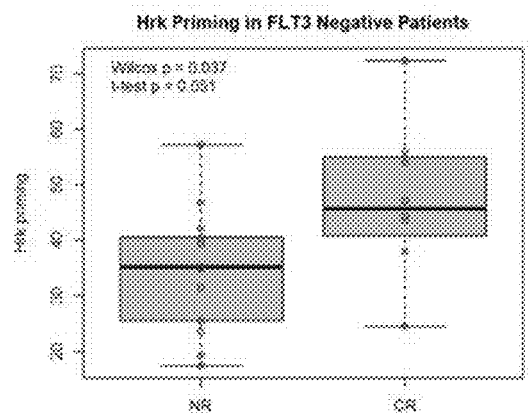
Figure 12C:
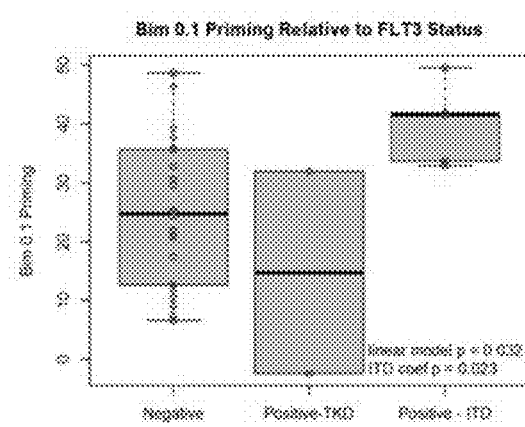
Figure 12D:
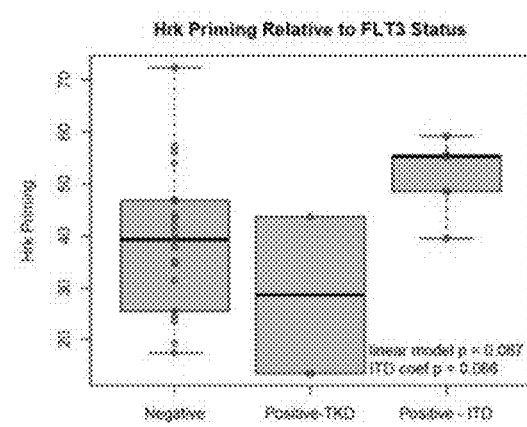

Patients treated with the hypomethylating agent, decitabine, were examined. These patients were previously characterized for several mutational characteristics including FLT3 abnormalities. Examination of these profiles with mutational statuses indicated that combination of FLT3 mutational status with the assay readout was necessary, as AML patients having FLT3 mutations were found to be non-responsive to decitabine in general, regardless of their mitochondrial profiling levels. However, in patients with unmutated FLT3, the BIM (0.1) peptide was found to be associated with response (FIG. 11A). Further, FLT3 mutation negative patients who responded to decitabine treatment showed significantly higher mitochondrial response to BH3 mimetics, BIM 0.1 ($p=0.04$) compared with those who did not respond. Patients with FLT3 mutations had significantly ($p=0.02$) higher BIM 0.1 priming in general. This indicates that a combination of mutational status with results from BH3 profiling is able to predict which patients will respond well to decitabine with a high accuracy.

Example 6: Alternate Methods for Assessing MCL-1 Dependencies

Figure 9:
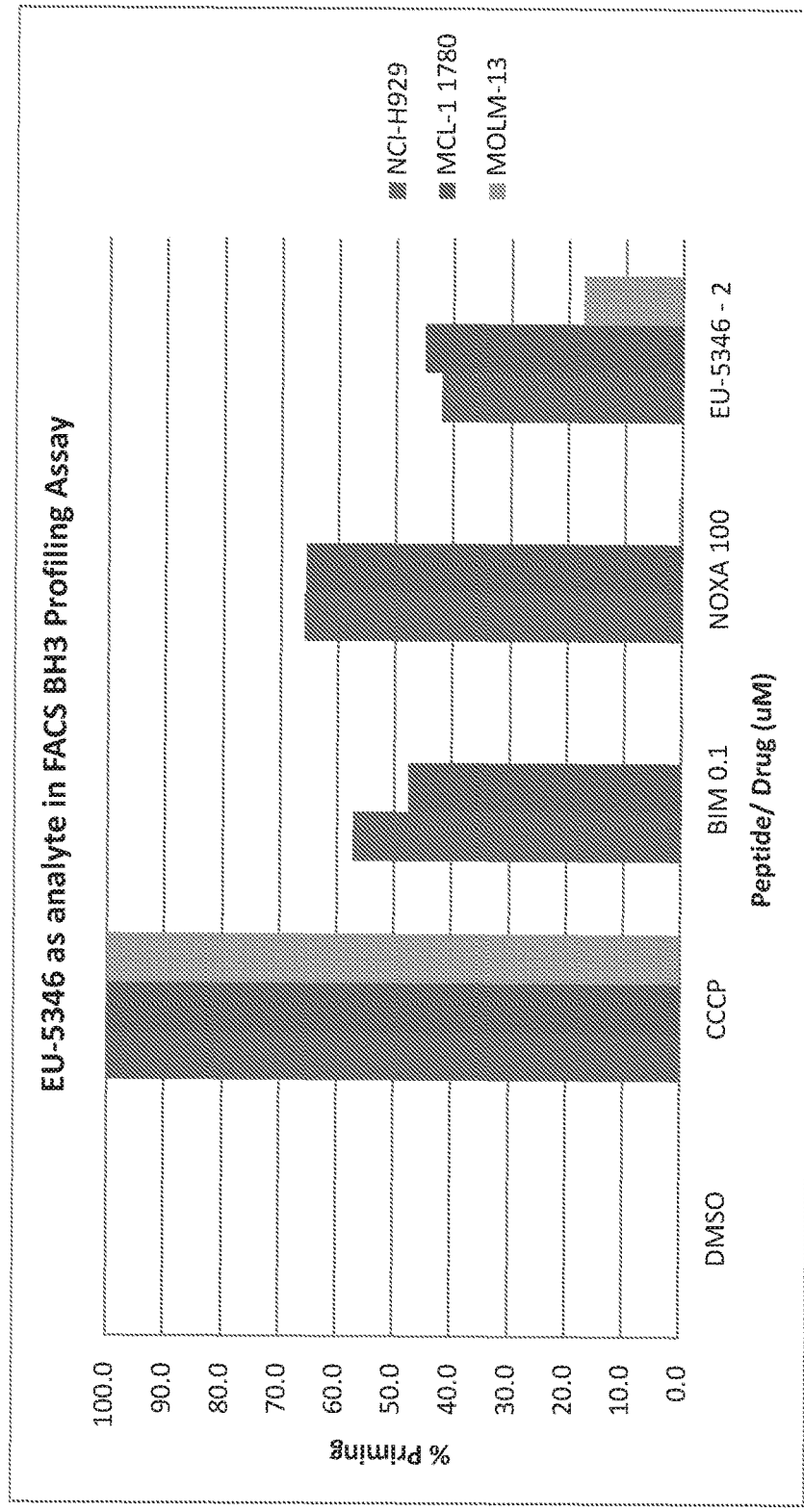
FIG. 9 shows that cell lines shown to be primed by NOXA are also responsive to an MCL-1 selective BH3 mimetic compound, EU5346 (Richard et al 2013) applied directly to permeabilized cells following the PraediCare Dx™ format. The mitochondrial response to the compound in three suspension cancer cell lines, represented as a priming value, indicates that EU5346 can be used as a ligand in the PraediCare Dx™ assay to detect NOXA priming.

To further probe MCL-1 dependencies we explored the utility of certain BH3 mimetic compounds to provide an alternative to the NOXA readout to determine MCL-1 dependency in cancer cells. Our approach was to directly apply membrane permeable BH3 mimetic compounds that selectively target MCL1. Doing so would add the advantage of directly observing on target activity of the therapeutic agent. FIG. 9 shows that cell lines that are primed by NOXA are also responsive to an MCL-1 selective BH3 mimetic compound, EU5346, applied directly to permeabilized cells following the PraediCare Dx™ format FACS BH3 profiling assay.

Those skilled in the art will recognize, or be able to ascertain, using no more than routine experimentation, numerous equivalents to the specific embodiments described specifically herein. Such equivalents are intended to be encompassed in the scope of the following claims.

REFERENCES

1. Rezaei, A., et al. "Leukemia Markers Expression of Peripheral Blood Vs Bone Marrow Blasts Using Flow Cytometry." *Med Sci Monit.* 9.8 (2003): 359-362.2.
2. Almarzooqi, S., et al. "Comparison of Peripheral Blood versus Bone Marrow Blasts Immunophenotype in Pediatric Acute Leukemias." *Ibnosina J Med BS* 195-204.
3. Zeng, Z., et al. "Targeting the Leukemia Microenvironment by CXCR4 Inhibition Overcomes Resistance to Kinase Inhibitors and Chemotherapy in AML." *Blood* 113.24 (2009): 6215-6224.
4. Yang, X. "Bone Marrow Stroma-mediated Resistance to FLT3 Inhibitors in FLT3-ITD AML Is Mediated by Persistent Activation of Extracellular Regulated Kinase." *Br J Haematol* 164.1 (2014): 61-72.
5. Mertens, D. & Stilgenbauer, S. Prognostic and predictive factors in patients with chronic lymphocytic leukemia: relevant in the era of novel treatment approaches? *Journal of clinical oncology* 32, 869-872, doi:10.1200/JCO.2013.53.8421 (2014).
6. Walter, R. B. et al. Effect of genetic profiling on prediction of therapeutic resistance and survival in adult acute myeloid leukemia. Leukemia 29, 2104-2107, doi: 10.1038/leu.2015.76 (2015).
7. Bannister T, Koenig M, He Y, et al. ML311: A Small Molecule that Potently and Selectively Disrupts the Protein-Protein Interaction of Mcl-1 and Bim: A Probe for Studying Lymphoid Tumorigenesis. Probe Reports from the NIH Molecular Libraries Program. Bethesda (Md.) 2010.

Tables

TABLE 1

| Patient Summary | |
|---|---|
| | # Pos/Total Number |
| Number of Patients | 63 |
| Median Age | 58 |
| Median BM Blast % | 38 |
| Median WBC Count at Diagnosis | 6020 |
| Adverse Cytogenetics | 26/63 |
| Intermediate Cytogenetics | 34/63 |
| Favorable Cytogenetics | 3/63 |
| FLT3 Mutation | 11/62 |
| NPM1 Mutation | 10/37 |
| MDS/Marrow Disorder History | 25/63 |
| Prior Chemo History | 7/63 |
| FLAM Treatment | 54/63 |
| Complete Remission | 29/63 |

TABLE 2

Patient Characteristics

| EIN | UPI | Protocol | Diagnosis | Source | Age | Cytogenetic Risk | FLT-3 | NPM1 | MDS/Marrow Disorder Hx | Prior Chemo Hx | % BM Blast | WBC at Dx | Tx | Response to Induction |
|---|---|---|---|---|---|---|---|---|---|---|---|---|---|---|
| 577 | 13566 | J0669 | AML | Marrow | 59 | INT | Neg | Not Done | Likely | No | 25 | 9880 | FLAM | CR |
| 580 | 13548 | J0669 | AML | Marrow | 61 | INT | Neg | Not Done | No | No | 20 | 1500 | FLAM | CR |
| 582 | 20866 | J0856 | AML | Blood | 49 | INT | Neg | Not Done | No | No | 6 | 2130 | FLAM | CR |
| 583 | 22844 | J0856 | Unknown | Blood | 57 | ADV | Neg | Neg | No | Yes | 13 | 2530 | FLAM | CR |
| 584 | 20345 | J0856 | Unknown | Marrow | 54 | INT | Neg | Not Done | Likely | No | 79 | 8030 | FLAM | CR |
| 585 | 21666 | J0856 | AML | Blood | 60 | INT | Pos (ITD) | Neg | No | No | 48 | 31330 | FLAM/IT Chemo | CR |
| 586 | 20566 | J0856 | AML | Marrow | 58 | ADV | Pos (ITD) | Pos | No | No | 94 | 39180 | FLAM | CR |
| 587 | 21845 | J0856 | AML | Marrow | 49 | FAV | Neg | Neg | No | No | 91 | 75630 | FLAM | CR |
| 589 | 21885 | J0856 | AML | Marrow | 53 | ADV | Neg | Neg | Yes | Yes | 5 | 2640 | FLAM | CR |
| 591 | 22228 | J0856 | AML | Marrow | 67 | ADV | Neg | Not Done | Yes | No | 58 | 890 | FLAM | CR |
| 597 | 19064 | J0856 | MDS | Marrow | 64 | INT | Neg | Neg | Yes | Yes | 13 | 10700 | FLAM | CR |
| 598 | 21905 | J0856 | AML | Blood | 59 | INT | Pos (ITD) | Neg | No | No | 71 | 103900 | FLAM | CR |
| 599 | 20725 | J0856 | AML | Blood | 52 | ADV | Neg | Not Done | Yes | No | 12 | 36990 | FLAM | CR |
| 603 | 22424 | J0856 | AML | Marrow | 73 | INT | Neg | Not Done | Yes | Yes | 83 | 10160 | FLAM | CR |
| 605 | 20284 | J0856 | AML | Blood | 54 | INT | Neg | Pos | No | No | 74 | 46690 | FLAM/IT Chemo | CR |
| 615 | 21905 | J1101 | AML | Blood | 59 | INT | Neg | Neg | No | No | 71 | 103900 | FLAM | CR |
| 620 | 2569 | J1101 | AML | Marrow | 69 | INT | Neg | Neg | Yes | No | 56 | 4580 | FLAM | CR |
| 621 | 2590 | J1101 | AML | Blood | 60 | INT | Neg | Neg | No | No | 10 | 25430 | FLAM | CR |
| 628 | 2453 | J1101 | AML | Blood | 63 | INT | Neg | Pos | Yes | No | 6 | 9350 | FLAM | CR |
| 631 | 2190 | J1101 | MDS | Marrow | 37 | INT | N/A | N/A | Yes | No | 12 | 1640 | FLAM | CR |
| 634 | 2526 | J1101 | AML | Blood | 57 | INT | Neg | Pos | No | No | | 71340 | FLAM | CR |
| 636 | 2539 | J1101 | AML | Marrow | 48 | INT | Neg | Neg | Yes | No | 12 | 1720 | FLAM | CR |
| 638 | 2671 | J1101 | AML | Marrow | 62 | INT | Neg | Neg | No | No | 47 | 2600 | 7 + 3 Ara C + Dauno | CR |
| 612 | 2754 | J1101 | AML | Marrow | 63 | ADV | Neg | Neg | No | No | 91 | 32130 | 7 + 3 Ara C + Dauno | Max RD |
| 624 | 2455 | J1101 | AML | Blood | 55 | ADV | Neg | Neg | Yes | No | 6 | 1870 | FLAM | Max RD |
| 588 | 20784 | J0856 | AML | Blood | 68 | INT | Pos (ITD) | Neg | No | No | 79 | 53580 | FLAM | MRD-F |
| 592 | 21627 | J0856 | AML | Blood | 51 | INT | Neg | Not Done | No | No | 70 | 420 | FLAM | MRD-F |
| 593 | 20744 | J0856 | AML | Marrow | 57 | INT | Neg | Not Done | Yes | No | 14 | 900 | FLAM | MRD-F |

TABLE 2-continued

Patient Characteristics

| EIN | UPI | Protocol | Diagnosis | Source | Age | Cytogenetic Risk | FLT-3 | NPM1 | MDS/Marrow Disorder Hx | Prior Chemo Hx | % BM Blast | WBC at Dx | Tx | Response to Induction |
|---|---|---|---|---|---|---|---|---|---|---|---|---|---|---|
| 607 | 20384 | J0856 | AML | Marrow | 52 | ADV | Neg | Not Done | Yes | No | 38 | 1440 | FLAM | MRD-F |
| 610 | 25524 | J1101 | AML | Marrow | 45 | ADV | Neg | Neg | Yes | Yes | 29 | 1560 | FLAM | MRD-F |
| 622 | 2578 | J1101 | AML | Marrow | 68 | ADV | Neg | Neg | No | No | 81 | 4900 | FLAM | MRD-F |
| 626 | 2561 | J1101 | AML | Blood | 58 | INT | Neg | Pos | No | No | 64 | 18930 | 7 + 3 Ara C + Dauno | MRD-M |
| 627 | 2669 | J1101 | MDS | Marrow | 65 | ADV | Neg | Neg | Yes | No | 1 | 17850 | FLAM | MRD-M |
| 630 | 2594 | J1101 | AML | Marrow | 57 | ADV | Neg | Neg | No | No | 71 | 1820 | FLAM | MRD-M |
| 596 | 22065 | J0856 | M6 | Blood | 71 | ADV | Neg | Not Done | No | No | 4 | 7080 | FLAM | PR-TD |
| 637 | 2747 | J1101 | AML | Marrow | 53 | INT | Neg | Pos | No | No | 25 | 1295 | FLAM | PR-TD |
| 590 | 18523 | J0856 | Unknown | Marrow | 50 | INT | Neg | Not Done | No | No | 81 | 6020 | FLAM | TF |
| 594 | 19123 | J0856 | AML | Marrow | 51 | ADV | Neg | Neg | No | No | 79 | 9920 | FLAM | TF |
| 595 | 20945 | J0856 | AML | Blood | 70 | ADV | Neg | Neg | No | No | 18 | 1830 | FLAM | TF |
| 601 | 20965 | J0856 | AML | Blood | 54 | INT | Neg | Neg | Likely | No | 17 | 1320 | FLAM | TF |
| 602 | 18843 | J0856 | AML | Marrow | 65 | ADV | Neg | Neg | Yes | Yes | 24 | 980 | FLAM | TF |
| 604 | 19085 | J0856 | AML | Marrow | 65 | FAV | Neg | Neg | No | No | 88 | 71670 | FLAM | TF |
| 606 | 20564 | J0856 | AML | Blood | 61 | INT | Neg | Neg | No | No | 89 | 37350 | FLAM | TF |
| 608 | 2328 | J1101 | AML | Blood | 67 | ADV | Neg | Neg | No | No | 66 | 2440 | 7 + 3 Ara C + Dauno | TF |
| 614 | 2514 | J1101 | AML | Blood | 58 | ADV | Neg | Neg | Yes | No | 3 | 1770 | 7 + 3 Ara C + Dauno | TF |
| 616 | 2653 | J1101 | AML | Marrow | 65 | ADV | Neg | Neg | No | No | 53 | 1100 | 7 + 3 Ara C + Dauno | TF |
| 619 | 2721 | J1101 | AML | Marrow | 63 | ADV | Neg | Neg | No | No | 28 | 4950 | FLAM | TF |
| 625 | 2708 | J1101 | AML | Marrow | 54 | ADV | Neg | Neg | No | No | 74 | 2610 | FLAM | TF |
| 629 | 2828 | J1101 | AML | Marrow | 53 | INT | Pos (ITD) | Pos | No | No | 96 | 64840 | FLAM | TF |
| 632 | 2792 | J1101 | AML | Unknown | 22 | ADV | Neg | Neg | No | No | 36 | 4130 | 7 + 3 Ara C + Dauno | TF |
| 633 | 2576 | J1101 | AML | Blood | 70 | INT | Neg | Neg | No | No | 32 | 3120 | FLAM | TF |
| 635 | 2167 | J1101 | AML | Marrow | 34 | INT | Pos (ITD) | Neg | No | No | 91 | 54300 | 7 + 3 Ara C + Dauno | TF |
| 576 | 22944 | J0669 | AML | Marrow | 56 | INT | Pos (D835) | Neg | yes | No | 39 | 47860 | FLAM | MRD-F |
| 578 | 13068 | J0669 | AML | Unknown | 51 | ADV | Neg | Not Done | Yes | Yes | 6 | 29740 | FLAM | CR |
| 579 | 13938 | J0669 | AML | Marrow | 70 | INT | Neg | Not Done | yes | no | 38 | 4030 | FLAM | CR |
| 581 | 14337 | J0669 | AML | Marrow | 66 | FAV | Pos(ITD) | Not Done | No | No | 87 | 11800 | FLAM | MRD-F |
| 600 | 20728 | J0856 | AML | Unknown | 54 | ADV | Neg | Neg | No | No | 58 | 10780 | FLAM | CR |
| 609 | 2280 | J1101 | MDS->AML | unknown | 51 | INT | Neg | Pos | Yes | No | 5 | 11710 | FLAM | CR |
| 611 | 2357 | J1101 | AML | Blood | 64 | INT | Neg | Pos | Yes | No | 79 | 3010 | 7 + 3 Ara C + Dauno | CR |
| 613 | 2414 | J1101 | AML | Blood | 68 | ADV | Neg | Neg | No | No | 24 | 1570 | FLAM | CR |

TABLE 2-continued

Patient Characteristics

| EIN | UPI | Protocol | Diagnosis | Source | Age | Cytogenetic Risk | FLT-3 | NPM1 | MDS/Marrow Disorder Hx | Prior Chemo Hx | % BM Blast | WBC at Dx | Tx | Response to Induction |
|---|---|---|---|---|---|---|---|---|---|---|---|---|---|---|
| 617 | 2415 | J1101 | AML | Blood | 61 | INT | Pos (ITD) | Neg | Yes | No | 13 | 7770 | FLAM | MRD-F |
| 618 | 2354 | J1101 | AML | Blood | 54 | ADV | Pos (ITD) | Neg | No | No | 32 | 6780 | FLAM | MRD-M |
| 623 | 2338 | J1101 | AML | Blood | 68 | ADV | Neg | Pos | No | No | 31 | 2080 | FLAM | TF |
| 576 | 22944 | J0669 | AML | Marrow | 56 | INT | Pos (D835) | Neg | yes | No | 39 | 47860 | FLAM | MRD-F |
| 578 | 13068 | J0669 | AML | Unknown | 51 | ADV | Neg | Not Done | Yes | Yes | 6 | 29740 | FLAM | CR |
| 579 | 13938 | J0669 | AML | Marrow | 70 | INT | Neg | Not Done | yes | no | 38 | 4030 | FLAM | CR |
| 581 | 14337 | J0669 | AML | Marrow | 66 | FAV | Pos(ITD) | Not Done | No | No | 87 | 11800 | FLAM | MRD-F |
| 600 | 20728 | J0856 | AML | Unknown | 54 | ADV | Neg | Neg | No | No | 58 | 10780 | FLAM | CR |
| 609 | 2280 | J1101 | MDS->AML | unknown | 51 | INT | Neg | Pos | Yes | No | 5 | 11710 | FLAM | CR |
| 611 | 2357 | J1101 | AML | Blood | 64 | INT | Neg | Pos | Yes | No | 79 | 3010 | 7 + 3 Ara C + Dauno | CR |
| 613 | 2414 | J1101 | AML | Blood | 68 | ADV | Neg | Neg | No | No | 24 | 1570 | FLAM | CR |
| 617 | 2415 | J1101 | AML | Blood | 61 | INT | Pos (ITD) | Neg | Yes | No | 13 | 7770 | FLAM | MRD-F |
| 618 | 2354 | J1101 | AML | Blood | 54 | ADV | Pos (ITD) | Neg | No | No | 32 | 6780 | FLAM | MRD-M |
| 623 | 2338 | J1101 | AML | Blood | 68 | ADV | Neg | Pos | No | No | 31 | 2080 | FLAM | TF |

TABLE 3

Clinical Characteristics Associations with Response

| Metric | Median NR (n = 29) | Median CR (n = 23) | Mann-Whitney p-value | Logistic Reg p-value | AUC |
|---|---|---|---|---|---|
| Age | 59 | 58 | 0.740 | 0.954 | 0.527 |
| WBC Count at Dx | 3120 | 9880 | 0.078 | 0.112 | 0.643 |
| BM Blast % | 53 | 36 | 0.296 | 0.332 | 0.586 |
| Cytogenetic Risk | — | — | 0.024 | 0.024 | 0.663 |
| NPM Mutation | — | — | 0.295 | 0.268 | 0.571 |
| FLT3 Mutation | — | — | 0.287 | 0.259 | 0.557 |
| MDS Marrow Disorder History | — | — | 0.144 | 0.132 | 0.601 |
| Protocol Followed | — | — | 0.060 | 0.038 | 0.637 |

TABLE 4

BH3 Profiling Data

| EIN | Viable Cell# | % Viability | % Blast | DMSO/ CCCP | BIM 100 μM | BIM 0.1 μM | PUMA 10 μM | NOXA 100 μM | BAD 100 μM | HRK 100 μM | BID 10 μM |
|---|---|---|---|---|---|---|---|---|---|---|---|
| 577 | 1.84E+07 | 67.2 | 16.00 | 124.80 | 32.92 | 5.65 | 12.11 | 55.03 | 18.14 | 63.42 | 7.52 |
| 580 | 3.20E+06 | 66.7 | 9.80 | 206.00 | 99.88 | 76.93 | 88.41 | 61.23 | 21.47 | 44.83 | 84.47 |
| 582 | 6.40E+06 | 99.1 | 35.20 | 95.50 | 97.85 | 28.93 | 49.81 | 0.00 | 34.24 | 13.10 | 22.74 |
| 583 | 5.00E+06 | 96.2 | 10.38 | 19.50 | 99.10 | 68.30 | 85.70 | 88.50 | — | 92.70 | 96.30 |
| 584 | 3.13E+06 | 81.5 | 12.14 | 76.18 | — | 19.91 | 33.45 | 45.55 | 2.89 | 54.70 | — |
| 585 | 5.40E+06 | 76.1 | 11.95 | 50.26 | 10.76 | 30.50 | 5.20 | 0.00 | 49.41 | 28.09 | 0.00 |
| 586 | 3.00E+06 | 61.2 | 16.58 | 35.75 | — | 36.60 | 33.30 | 69.70 | 63.00 | 28.50 | 49.20 |
| 587 | 1.14E+08 | 82.6 | 38.00 | 62.13 | 99.02 | 68.89 | 67.81 | 44.48 | 72.20 | 73.92 | 83.78 |
| 589 | 1.85E+07 | 94.9 | 19.00 | 424.30 | 100.06 | 49.13 | 83.99 | 17.22 | 79.91 | 82.17 | 76.90 |
| 591 | 7.20E+06 | 61.0 | 17.00 | 20.70 | 38.96 | 8.46 | 9.66 | 55.30 | 24.31 | — | — |
| 597 | 1.33E+07 | 55.6 | 11.00 | 40.50 | 26.02 | 0.00 | 0.17 | 46.15 | 75.58 | 33.39 | 0.00 |
| 598 | 7.69E+07 | 91.6 | 29.75 | 58.50 | 99.20 | 65.40 | 65.30 | 0.10 | 70.10 | 64.90 | 69.90 |
| 599 | 3.95E+07 | 92.1 | 30.68 | 357.84 | 99.50 | 10.10 | 34.60 | 0.90 | 11.70 | 25.50 | 16.00 |
| 603 | 5.12E+07 | 79.0 | 36.00 | 168.08 | 67.76 | 12.82 | 43.18 | 11.64 | 45.94 | 22.34 | 16.80 |
| 605 | 5.84E+06 | 94.8 | 25.00 | 72.01 | 99.70 | 28.20 | 49.60 | 27.70 | 35.40 | 59.70 | 66.60 |
| 615 | 1.20E+07 | 91.1 | 46.46 | 178.42 | 100.00 | 10.70 | 40.20 | 4.50 | 23.80 | 11.80 | 12.50 |
| 620 | 4.00E+06 | 85.1 | 8.50 | 200.71 | 99.95 | 8.69 | 53.68 | 10.89 | 49.64 | 14.12 | 2.13 |
| 621 | 9.00E+06 | 80.0 | 37.04 | 63.60 | 100.17 | 49.49 | 71.69 | 25.03 | 56.90 | 56.11 | 74.89 |
| 628 | 8.60E+06 | 84.3 | 22.60 | 78.56 | 100.98 | 14.46 | 67.70 | 9.81 | 66.95 | 36.62 | 19.85 |
| 631 | 2.70E+06 | 62.8 | 6.60 | 60.52 | 76.37 | 30.91 | 33.77 | 14.43 | 44.87 | 7.15 | 7.22 |
| 634 | 8.70E+06 | 95.6 | 55.14 | 57.02 | 100.10 | 57.40 | 74.40 | 26.80 | 61.30 | 77.50 | 87.30 |
| 636 | 1.40E+07 | 63.0 | 38.97 | 25.76 | 98.60 | 47.00 | 84.40 | 0.00 | — | 0.00 | 96.90 |
| 638 | 1.12E+07 | 97.4 | 8.90 | 563.30 | 100.02 | 14.23 | 18.52 | 13.90 | 6.79 | 5.40 | 6.77 |
| 612 | 4.00E+07 | 92.6 | 11.72 | 487.02 | 100.00 | 14.40 | 50.90 | 0.00 | 55.30 | 7.80 | 23.60 |
| 624 | 2.40E+07 | 75.0 | 5.50 | 285.60 | 99.48 | 68.16 | 67.25 | 64.74 | 51.71 | 79.78 | 70.48 |
| 588 | 1.27E+07 | 95.2 | 59.52 | 20.98 | 96.10 | 62.00 | 69.30 | 21.40 | 68.60 | 81.50 | 85.40 |
| 592 | 1.90E+06 | 63.3 | 6.37 | 23.93 | 91.60 | 24.70 | 36.10 | 53.50 | 91.10 | 65.50 | 37.10 |
| 593 | 2.80E+06 | 58.3 | 15.00 | 235.54 | 100.16 | 68.96 | 80.06 | 21.66 | 77.15 | 77.34 | 72.75 |
| 607 | 7.36E+07 | 83.6 | 54.48 | 390.31 | 97.67 | 19.87 | 40.24 | 18.96 | 40.98 | 23.63 | 15.85 |
| 610 | 1.05E+06 | 26.2 | 15.60 | 73.20 | 58.50 | 2.72 | — | — | — | — | — |
| 622 | 7.70E+06 | 79.4 | 19.72 | 78.63 | 100.98 | 14.46 | 67.70 | 9.81 | 66.95 | 36.62 | 19.85 |
| 626 | 2.06E+06 | 97.6 | 65.40 | 477.90 | 100.00 | 64.70 | 88.60 | 0.00 | 85.00 | 63.00 | 69.80 |
| 627 | 8.00E+06 | 97.6 | 10.75 | 120.50 | 99.80 | 25.10 | 55.10 | 0.00 | 5.70 | 12.20 | 76.80 |
| 630 | 1.43E+07 | 92.9 | 27.00 | 264.46 | 100.00 | 0.00 | 46.97 | 0.60 | 49.36 | 0.00 | 0.00 |
| 596 | 2.02E+06 | 92.2 | 28.82 | 104.71 | 99.70 | 46.10 | 66.40 | 30.90 | 48.60 | 71.70 | 80.30 |
| 637 | 7.20E+06 | 90.0 | 18.47 | 124.44 | 94.50 | 66.93 | — | — | — | — | — |
| 590 | 4.40E+07 | 88.7 | 32.00 | 332.63 | 99.90 | 11.13 | 81.72 | 3.65 | 79.12 | 18.72 | 9.74 |
| 594 | 3.30E+07 | 79.3 | 36.00 | 302.16 | 100.27 | 34.73 | 73.89 | 10.78 | 72.09 | 34.02 | 19.44 |
| 595 | 6.00E+06 | 67.4 | 10.24 | 23.17 | 18.40 | 0.00 | 19.50 | 33.00 | 97.50 | 7.60 | 0.00 |
| 601 | 7.90E+06 | 88.8 | 6.01 | 79.21 | 89.70 | 26.60 | 46.20 | 38.90 | 55.00 | 46.50 | 52.40 |
| 602 | 1.08E+07 | 72.5 | 27.00 | 357.00 | 98.00 | 0.00 | 20.69 | 0.00 | 33.61 | 33.68 | 11.78 |
| 604 | 6.40E+07 | 76.2 | 36.00 | 45.36 | 99.82 | 35.90 | 45.18 | 22.75 | 25.21 | 45.64 | 39.31 |
| 606 | 1.50E+06 | 65.2 | 11.00 | 95.28 | 100.01 | 85.07 | 92.94 | 93.99 | — | — | — |
| 608 | 7.10E+06 | 72.4 | 30.95 | 308.70 | 99.23 | 70.83 | 88.60 | 45.57 | 92.23 | 55.45 | 62.87 |
| 614 | 5.10E+06 | 68.9 | 6.07 | 17.94 | 98.70 | 43.20 | 67.00 | 0.00 | 82.40 | 71.60 | 58.40 |
| 616 | 1.18E+07 | 87.4 | 25.90 | 253.16 | 99.97 | 0.00 | 63.31 | 0.50 | 61.17 | 10.21 | 7.15 |
| 619 | 7.20E+06 | 82.8 | 15.65 | 208.03 | 99.90 | 31.40 | 40.20 | 5.20 | 9.00 | 50.20 | 61.20 |
| 625 | 6.20E+06 | 87.3 | 41.40 | 221.00 | 99.98 | 15.46 | 27.28 | 23.28 | 34.50 | 27.36 | 14.28 |
| 629 | 1.11E+07 | 94.1 | 36.00 | 148.87 | 99.79 | 44.04 | 73.69 | 25.24 | 76.93 | 50.35 | 33.93 |
| 632 | 1.15E+07 | 93.5 | 22.00 | 371.06 | 99.95 | 5.81 | 33.53 | 0.00 | 3.12 | 9.00 | 19.16 |
| 633 | 6.50E+06 | 85.5 | 8.68 | 229.99 | 99.70 | 29.00 | 64.00 | 47.20 | 55.20 | 60.30 | 57.90 |
| 635 | 2.00E+05 | 83.3 | 36.00 | 280.90 | — | 18.94 | — | — | — | — | — |

TABLE 5

Associations of Individual BH3 Peptide Profiles with CR

| Metric | Median NR (n = 29) | Median CR (n = 23) | Mann-Whitney p-value | Logistic Reg p-value | AUC |
| --- | --- | --- | --- | --- | --- |
| BAD | 55.3 | 45.9 | 0.090 | 0.084 | 0.647 |
| BID | 37.1 | 22.7 | 0.843 | 0.767 | 0.517 |
| BIM 0.1 | 26.6 | 28.9 | 0.927 | 0.975 | 0.507 |
| BIM 100 | 99.8 | 99.2 | 0.461 | 0.094 | 0.562 |
| NOXA | 20.2 | 17.2 | 0.394 | 0.445 | 0.571 |
| PUMA | 63.7 | 49.6 | 0.229 | 0.156 | 0.600 |
| HRK | 45.6 | 35 | 0.915 | 0.943 | 0.509 |

TABLE 6

Multivariate Analysis of BH3 Peptide Profiling with Other Clinical Variables

| Metric | Median NR (n = 29) | Median CR (n = 23) | Mann-Whitney p-value | Logistic Reg p-value | AUC |
| --- | --- | --- | --- | --- | --- |
| Cytogenetic Risk | — | — | 0.024 | 0.024 | 0.663 |
| MDS Marrow Disorder History | — | — | 0.144 | 0.132 | 0.601 |
| BAD | 55.3 | 45.9 | 0.09 | 0.084 | 0.647 |
| BIM 100 | 99.8 | 99.2 | 0.461 | 0.094 | 0.562 |
| PUMA | 63.7 | 49.6 | 0.229 | 0.156 | 0.6 |
| BAD + BIM 100 + PUMA | — | — | 0.009 | 0.039 | 0.732 |
| BAD + BIM 100 + PUMA + Cytogenetics | — | — | 0.0001 | 0.003 | 0.84 |
| BAD + BIM 100 + PUMA + Cytogenetics + MDS History | — | — | 0.0001 | 0.002 | 0.851 |
| NOXA | 20.2 | 17.2 | 0.394 | 0.445 | 0.571 |
| NOXA + Cytogenetics | — | — | 0.024 | 0.054 | 0.689 |
| NOXA + Cytogenetics + MDS History | — | — | 0.004 | 0.024 | 0.739 |

TABLE 7

Associations of Individual BH3 Peptide Profiles with CR in Bone Marrow Samples

| Metric | Median NR (n = 18) | Median CR (n = 13) | Mann-Whitney p-value | Logistic Reg p-value | AUC |
| --- | --- | --- | --- | --- | --- |
| BAD | 49.4 | 45.4 | 0.719 | 0.695 | 0.544 |
| BID | 19.4 | 16.8 | 0.917 | 0.368 | 0.512 |
| BIM 0.1 | 17.2 | 19.9 | 0.535 | 0.430 | 0.566 |
| BIM 100 | 99.9 | 98.6 | 0.067 | 0.012 | 0.709 |
| NOXA | 5.2 | 44.5 | 0.006 | 0.0007 | 0.805 |
| PUMA | 50.9 | 33.8 | 0.339 | 0.275 | 0.610 |
| HRK | 27.4 | 30.9 | 0.714 | 0.461 | 0.542 |

TABLE 8

Statistical analyses of BH3 peptides were performed in only those samples that were obtained from bone marrow

| Metric | Median NR (n = 18) | Median CR (n = 13) | Mann-Whitney p-value | Logistic Reg p-value | AUC |
| --- | --- | --- | --- | --- | --- |
| BAD | 49.4 | 45.4 | 0.719 | 0.695 | 0.544 |
| BIM 100 | 99.9 | 98.6 | 0.067 | 0.012 | 0.709 |
| PUMA | 50.9 | 33.8 | 0.339 | 0.275 | 0.61 |
| BAD + BIM 100 + PUMA | — | — | 0.008 | 0.0058 | 0.813 |
| BAD + BIM 100 + PUMA + Cytogenetics | — | — | 0.0007 | 0.0051 | 0.887 |
| BAD + BIM 100 + PUMA + Cytogenetics + MDS History | — | — | 0.001 | 0.0069 | 0.893 |
| NOXA | 5.2 | 44.5 | 0.006 | 0.0007 | 0.805 |
| NOXA + Cytogenetics | — | — | 0.0008 | 0.0015 | 0.874 |
| NOXA + Cytogenetics + MDS History | — | — | 0.0002 | 0.0002 | 0.918 |

---

What is claimed is:

1. A method for selecting a patient having acute myelogenous leukemia (AML) for treatment, comprising:
   a) permeabilizing an aliquot of cells obtained from a bone marrow aspirate of the patient, and permeabilizing an aliquot of cells from peripheral blood of the patient;
   b) contacting the aliquot of permeabilized bone marrow aspirate cells with a NOXA peptide, wherein the NOXA peptide comprises the amino acid sequence of SEQ ID NO: 1, and contacting the aliquot of permeabilized peripheral blood with a BIM peptide;
   c) measuring NOXA peptide-induced mitochondrial outer membrane permeabilization (MOMP) in the aliquot of bone marrow aspirate cells, and measuring BIM peptide-induced MOMP in the aliquot of permeabilized peripheral blood, to determine a percent priming for the NOXA peptide and the BIM peptide, as defined by the following equation:

$$\% \text{ Priming} = \left(1 - \frac{((\text{Peptide}) \, AUC - CCCP \, AUC)}{(DMSO \, AUC - CCCP \, AUC)}\right) \times 100$$

wherein:
   the Peptide AUC comprises either an area under a curve or a signal intensity of the NOXA peptide, or the BIM peptide,
   the CCCP (Carbonyl cyanide m-chlorophenyl hydrazone) AUC comprises either an area under a curve or a signal intensity of a baseline positive control, and
   the DMSO AUC comprises either an area under a curve or a signal intensity of a baseline negative control,
   d) comparing the percent priming of the NOXA peptide and the BIM peptide, and selecting the patient as suitable for therapy if the NOXA percent priming is greater than about 10% and the BIM percent priming is less than about 35%; and
   e) administering a therapy comprising alvocidib to the selected patient of step (d).

2. The method of claim 1, wherein the method further comprises predicting a clinical response in the patient.

3. The method of claim 2, wherein the clinical response is at least about 1, about 2, about 3, or about 5 year progression/event-free survival.

4. The method of claim 1, wherein the area under the curve for the NOXA AUC, BIM AUC, CCCP AUC, and DMSO AUC are each established by homogenous time-resolved fluorescence (HTRF).

5. The method of claim 1, wherein the signal intensity for the NOXA AUC, BIM AUC, CCCP AUC, and DMSO AUC are each a single time point measurement that occurs over a window from between about 0 to about 300 min to about 0 to about 30 min.

6. The method of claim 1, wherein the area under the curve for the NOXA AUC, BIM AUC, CCCP AUC, and DMSO AUC are each established by fluorescence activated cell sorting (FACS).

7. The method of claim 1, wherein the signal intensity for the NOXA AUC, BIM AUC, CCCP AUC, and DMSO AUC are each a single time point measurement that occurs between about 5 min and about 300 min.

8. The method of claim 1, wherein the patient is evaluated for a risk factor selected from age, cytogenetic risk classification, FMS-like tyrosine kinase-3 (FLT-3) mutation status, nucleophosmin 1 (NPM1) mutation status, MDS/Marrow Disorder History, prior chemotherapy history, Bone Marrow (BM) Blast %, and White Blood Cell (WBC) Count at Diagnosis.

9. The method of claim 1, wherein the BIM peptide is at a concentration of 0.1 µM in the BIM peptide-induced MOMP aliquot.

* * * * *

SEQUENCE LISTING

```
<160> NUMBER OF SEQ ID NOS: 2

<210> SEQ ID NO 1
<211> LENGTH: 20
<212> TYPE: PRT
<213> ORGANISM: Homo sapiens

<400> SEQUENCE: 1

Ala Glu Leu Pro Pro Glu Phe Ala Ala Gln Leu Arg Lys Ile Gly Asp
1               5                   10                  15

Lys Val Tyr Cys
            20

<210> SEQ ID NO 2
<211> LENGTH: 55
<212> TYPE: PRT
<213> ORGANISM: Homo sapiens

<400> SEQUENCE: 2

Met Pro Gly Lys Lys Ala Arg Lys Asn Ala Gln Pro Ser Pro Ala Arg
1               5                   10                  15

Ala Pro Ala Glu Leu Pro Pro Glu Phe Ala Ala Gln Leu Arg Lys Ile
            20                  25                  30
```

```
Gly Asp Lys Val Tyr Cys Phe Arg Gln Lys Leu Leu Asn Leu Ile Ser
        35                  40                  45
Lys Leu Phe Cys Ser Gly Thr
 50              55
```